United States Patent
Lee et al.

(10) Patent No.: US 10,589,270 B2
(45) Date of Patent: Mar. 17, 2020

(54) DIGITAL FLUID SAMPLE SEPARATION APPARATUS AND METHODS FOR ONE-STEP QUANTITATIVE SAMPLE ANALYSIS

(71) Applicant: THE REGENTS OF THE UNIVERSITY OF CALIFORNIA, Oakland, CA (US)

(72) Inventors: Luke P. Lee, Orinda, CA (US); Erh-Chia Yeh, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 715 days.

(21) Appl. No.: 15/017,851

(22) Filed: Feb. 8, 2016

(65) Prior Publication Data
US 2016/0228874 A1    Aug. 11, 2016

Related U.S. Application Data

(63) Continuation of application No. PCT/US2014/050413, filed on Aug. 8, 2014.
(Continued)

(51) Int. Cl.
*B01L 3/00* (2006.01)
*C12Q 1/6806* (2018.01)
(Continued)

(52) U.S. Cl.
CPC ...... *B01L 3/502753* (2013.01); *C12Q 1/6806* (2013.01); *C12Q 1/689* (2013.01);
(Continued)

(58) Field of Classification Search
CPC ..... A61B 5/746; A61B 5/7292; A61B 5/7289; A61B 5/7275; A61B 5/00; A61B 5/7282;
(Continued)

(56) References Cited

U.S. PATENT DOCUMENTS

2004/0129678 A1  7/2004  Crowley et al.
2009/0107909 A1  4/2009  Kotera
(Continued)

FOREIGN PATENT DOCUMENTS

CN    101454664 A    6/2009
CN    103074203 A    5/2013
(Continued)

OTHER PUBLICATIONS

Korean Intellectual Property Office, International Search Report and Written Opinion, PCT/US2014/050413, dated Nov. 18, 2014, pp. 1-10, with claims searched, pp. 11-15. The application filed herewith is a continuation of PCT/US2014/050413.
(Continued)

*Primary Examiner* — Samuel P Siefke
(74) *Attorney, Agent, or Firm* — O'Banion & Ritchey LLP; John P. O'Banion

(57) ABSTRACT

A Digital Separation (DS) chip for separating, digitizing and analyzing a fluid sample is presented. The DS chip includes a fluidic layer that prepares and compartmentalizes the fluid sample for analysis. Cliff structures that are adjacent to wells skim the fluid sample and prevent particles, which may interfere with fluid sample analysis, from entering the wells. Skimmed fluid sample analysis occurs in the wells and endpoint data can be collected and used to determine an original concentration of a desired component in the fluid sample very quickly. Using the described apparatus and methods, a fluid sample can be prepared, digitized, compartmentalized, assayed and the endpoint data collected in ~30 minutes. The apparatus and methods can easily be adapted to provide parallel processing of a sample.

19 Claims, 19 Drawing Sheets

Related U.S. Application Data

(60) Provisional application No. 61/864,346, filed on Aug. 9, 2013.

(51) Int. Cl.

| | | |
|---|---|---|
| *C12Q 1/6851* | (2018.01) | |
| *C12Q 1/689* | (2018.01) | |
| *C12Q 1/70* | (2006.01) | |
| *B01L 7/00* | (2006.01) | |
| *G01N 35/00* | (2006.01) | |

(52) U.S. Cl.
CPC ........... *C12Q 1/6851* (2013.01); *C12Q 1/703* (2013.01); *B01L 7/52* (2013.01); *B01L 2200/0684* (2013.01); *B01L 2200/10* (2013.01); *B01L 2300/0681* (2013.01); *B01L 2300/0816* (2013.01); *B01L 2300/0864* (2013.01); *B01L 2300/0883* (2013.01); *B01L 2300/0887* (2013.01); *B01L 2400/0406* (2013.01); *B01L 2400/049* (2013.01); *B01L 2400/0481* (2013.01); *C12Q 2565/629* (2013.01); *C12Q 2600/158* (2013.01); *G01N 2035/00158* (2013.01)

(58) Field of Classification Search
CPC .... G08B 21/0453; G08B 21/02; G08B 25/14; G06F 19/00; G16H 50/20; B01L 3/502753; B01L 2200/0684; B01L 2300/0816; B01L 2300/0883; B01L 2400/0406; B01L 2300/0681; B01L 7/52; B01L 2400/049; B01L 2400/0481; B01L 2300/0887; B01L 2200/10; B01L 2300/0864; C12Q 1/6851; C12Q 1/703; C12Q 1/689; C12Q 1/6806; C12Q 2565/629; C12Q 2600/158; G01N 2035/00158
See application file for complete search history.

(56) References Cited

U.S. PATENT DOCUMENTS

| | | |
|---|---|---|
| 2010/0140171 A1 | 6/2010 | Heath |
| 2011/0236264 A1 | 9/2011 | Rajagopal |
| 2012/0276641 A1 | 11/2012 | Dimov et al. |
| 2013/0102062 A1 | 4/2013 | Kojima et al. |
| 2013/0130232 A1 | 5/2013 | Weibel et al. |

FOREIGN PATENT DOCUMENTS

| | | |
|---|---|---|
| EP | 2020598 A1 | 2/2009 |
| JP | 2008188124 A | 8/2008 |
| WO | 2004048254 A1 | 6/2004 |
| WO | 2009017627 A1 | 2/2009 |
| WO | 2011/051405 A1 | 5/2011 |
| WO | 2017062864 | 4/2017 |

OTHER PUBLICATIONS

Ho et al., "Rapid identification of ESKAPE bacterial strains using an autonomous microfluidic device", Plos One, vol. 7, Issue 7, article No. 341245, pp. 1-7, Jul. 27, 2012.
Cira et al., "A self-loading microfluidic device for determining the minimum inhibitory concentration of antibiotics", Lab on a Chip, vol. 12, pp. 1052-1059, Mar. 21, 2012.
Dimov et al., "Stand-alone self powered integrated microfluidic blood analysis system (SIMBAS)", Lab on a Chip, vol. 11, pp. 845-850, Mar. 7, 2011.
Yeh et al., "One-step digital plasma separation for molecular diagnostics", In: 17th International Conference on Miniaturized Systems for Chemistry and Life Sciences, Freiburg, Germany, pp. 1323-1325, Oct. 27-31, 2013.
European Patent Office (EPO), Office Action (communication pursuant to Article 94(3) EPC) dated May 23, 2018, related European Patent Application No. 14834471.6, pp. 1-6, claims examined, pp. 7-10.
Korean Intellectual Property Office (KIPO), International Search Report and Written Opinion dated Jan. 11, 2017, related PCT international applicaiton No. PCT/US2016/056127, pp. 1-12, claims searched, pp. 13-21.
State Intellectual Property Office of the P.R.C., Official Action dated Oct. 18, 2017, related Chinese Patent Application No. CN201480049865.5, pp. 1-14, English-language translation, pp. 15-30, claims examined, pp. 31-35.
State Intellectual Property Office of the P.R.C., Official Action dated Apr. 21, 2017, related Chinese Patent Application No. CN201480049865.5, pp. 1-13, English-language translation, pp. 14-23, claims examined, pp. 15-28.
European Patent Office (EPO), European Search Report dated May 18, 2017, related European Patent Application No. 14834471.6, pp. 1-10, with claims searched, pp. 11-15.
Grafton, Meggie M.G. et al., "Microfluidic MEMS Hand-Held Flow Cytometer", Microfluidics, BioMEMS, and Medical Microsystems IX, Proc. of SPIE, vol. 7929, No. 1, Feb. 10, 2011, pp. 1-10.
Wang, Li et al., "Self-loading and cell culture in one layer microfluidic devices", Biomed Microdevices (2009) 11:679-684, published online Jan. 9, 2009.
Liang, David Y. et al., "Systematic characterization of degas-driven flow for poly(dimethlsiloxane) microfluidic devices", American Institute of Physics, Biomicrofluidics, vol. 5, No. 2, 024108 (2011), published Jun. 1, 2011.
Yeh, Erh-Chia et al., "A Single-Step Digital Nucleic Acid Amplification Platform by Digital Plasma Separation on a Chip", Biophysical Journal, vol. 106, No. 2, 2100, Board B830, Feb. 17, 2014.
State Intellectual Property Office of The P.R.C., Official Action dated Sep. 6, 2016, related Chinese Patent Application No. CN201480049865.5, pp. 1-12, English-language translation, pp. 13-20, claims examined, pp. 21-25. The relevance of non-English language reference CN103074203 is indicated therein, and US2013/0102062 is an English-language equivalent.

DIGITAL FLUID SAMPLE SEPARATION APPARATUS AND METHODS FOR ONE-STEP QUANTITATIVE SAMPLE ANALYSIS

CROSS-REFERENCE TO RELATED APPLICATIONS

This application is a 35 U.S.C. § 111(a) continuation of PCT international application number PCT/US2014/050413 filed on Aug. 8, 2014, incorporated herein by reference in its entirety, which claims priority to, and the benefit of, U.S. provisional patent application Ser. No. 61/864,346 filed on Aug. 9, 2013, incorporated herein by reference in its entirety. Priority is claimed to each of the foregoing applications.

The above-referenced PCT international application was published as PCT International Publication No. WO 2015/021425 on Feb. 12, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND

1. Technical Field

This invention pertains generally to one-step sample preparation and analysis, and more particularly to the integration of suspension separation, multiplexed compartmentalization and digital amplification and/or detection of components within the separated solution, where the system may be automated using degas driven flow.

2. Background Discussion

Real-time PCR is currently the standard method for quantitative nucleic acid (NA) detection in body fluid samples. Viral load, or the quantity of virus in an organism (usually blood), is one of the most essential markers for indicating the effectiveness of antiviral therapy and disease progression. Conventional HIV viral load monitoring tests, approved by the US Food and Drug Administration, use real-time polymerase chain reaction (real-time PCR) assays. This method typically involves expensive equipment, such as real-time thermal cyclers, 2-3 hours of assay time, multiple manual steps requiring trained technicians, and the need for sample preparation to remove contaminants. For example, in standard real-time PCR assays, a sample such as blood needs to be purified since hemoglobin and IgG can inhibit polymerase activity as their chelating nature disrupts $Fe^{3+}$ concentration.

Since blood cells can interfere with diagnostic assays by obstructing the optical detection path by its opaqueness, plasma separation is a common step for blood based protein and other sample component diagnostics. Hemoglobin released from lysed red blood cells can inhibit other enzyme reactions by chelating ions and therefore it is desirable to remove blood cells prior to conducting almost all assays.

Sample purification may be done with phenol/chloroform extraction or silica spin columns. The standard plasma separation technique is via centrifugation, which requires electrical sources and bulky equipment. Membrane filter and mechanical filter methods are also popular; however, they often clog or cause hemolysis. Other methods that utilize hydrodynamic lift force, Zweifach-Fung effect or inertia forces require external pumps to control flow rates precisely. Active separation using external fields such as acoustics, electro-osmotic flow, and magnetic forces have been used. However, these separations also require external power sources, have highly complex chip design, and require external equipment.

There are also sedimentation methods, such as cross flow-filtration, sedimentation in a plug and gravity induced lamination. The main advantage of these sedimentation systems is the significant reduction in hemolysis because of the low shear stress on red blood cells. However, of all the discussed purification or separation methods, there has yet to be a coupling of these technologies and sample compartmentalization for a rapid one-step digital fluid sample analysis.

Other NA assays, such as transcription-mediated amplification or branched-DNA tests, can be used but suffer from the same constraints as real-time PCR, requiring multiple steps of sample preparation, approximately 3 to 6 hours of assay time and highly trained technicians. Furthermore, these techniques all require centralized laboratory testing and, therefore, samples have to be transported, which can result in sample degradation. Centralization also limits the access for low resource sites that are far away.

Newer ELISA (Enzyme Linked Immunosorbent Assay) based techniques have also been developed. Although they can reduce the cost of testing (approximately $5 to $23) and are simpler assays to perform, they are still time consuming, requiring significant manual handling time (6 to 72 hours). The latest lateral flow strips have been shown to detect NA. However, multiple manual steps are still required and these assays generally provide qualitative but not quantitative NA detection.

It is desirable to combine rapid sample preparation and quantitative assay endpoint readout into the same diagnostic chip to simplify, reduce the cost and shorten the steps needed for fluid sample analysis.

BRIEF SUMMARY

Apparatus and methods are presented that provide an inexpensive, portable technology, which combines sample fluid separation (purification) and digital quantitative sample analysis readout into one fluidic design. According to one aspect of the disclosed technology, a whole blood sample can be processed for NA quantification (e.g. HIV viral load) in ~30 minutes.

In one step, the Digital Separation (DS) chip can automatically separate a sample suspension, distribute sample solution into more than 200 wells and compartmentalize samples for automatic digital isothermal NA amplification (e.g. Recombinase Polymerase Amplification (RPA)) in 10 minutes, without the need for external power sources. It should be appreciated that the DS chip can be used for assays other than isothermal NA amplification as well, such as quantitative protein analysis, immuno-assays, etc.

According to one aspect of the presently disclosed technology, degas driven flow may be used to move and distribute a fluid sample through the DS chip and therefore, no external power sources or pumps are required. The system may be completely portable. Additionally, the system can operate without an oil phase for compartmentalization for digital NA, protein, antibody, etc. detection. An air plug that follows after the receding liquid meniscus can automatically compartmentalize the wells.

According to another aspect of the presently disclosed technology, sample preparation (suspension separation) and digital sample analysis readout (sample compartmentalization) are integrated into one-step with the Digital Separation design.

According to another aspect of the presently disclosed technology, a cliff structure in the DS chip may enable consistent volume size during sample compartmentalization and may ensure minimal NA amplification, fluorescence interference, etc. from particles (e.g. red blood cells). For example, it has been shown that >95% of the blood cells can be removed with the cliff structures.

According to another aspect of the presently disclosed technology, there is no hemolysis or clogging with Digital Separation. This is a common problem with membrane filtration based methods. This can be important because, for example, hemoglobin from lysed red blood cells can significantly inhibit NA assays.

According to yet another aspect of the presently disclosed technology, very large numbers of wells (10 to 1500 wells, 30 to 100 nl/well) may be separated in ~10 minutes. Between 50 and 100 µl of fluid sample may be processed within 10 minutes, yielding 20 to 50 µl of digitized sample per well. The volume of separated sample can be easily tuned by scaling the number or size of the wells. Furthermore, this can be a high throughput system. Since only an endpoint reading is taken, many devices can be run in parallel as opposed to real-time PCR, which runs samples in serial since real-time data points are needed.

According to yet another aspect of the presently disclosed technology, total assay time may be less than 40 minutes with minimal manual operation necessary (loading samples, isothermal heat incubation and endpoint reading).

According to yet another aspect of the presently disclosed technology, the DS chip may function as a platform for isothermal NA amplification with a dynamic range of $10^3$ to $10^6$ copies/ml. The dynamic range can be customized by simply changing well size to control digitization. Other types of NA assays (isothermal, PCR, etc.) may be adopted for this platform technology, providing a unique combination of passive inertial separation and digital NA assays.

According to yet another aspect of the presently disclosed technology, the DS chip may be inexpensive to use since only very simple optics are required to analyze a sample. Endpoint digital readout can be done by a standard fluorescence microscope or smartphone with filters. No real-time imaging system is needed.

According to yet another aspect of the presently disclosed technology, auxiliary degas chambers may be integrated into the DS chip to increase the sample loading rate to less than 10 minutes. Another embodiment of the DS chip may integrate thumb pump microSIP technology where degas driven flow may not be feasible.

According to yet another aspect of the presently disclosed technology, the DS chip may have a shelf life of at least one year when stored in vacuum food packs. Storage in vacuum conditions stabilizes lyophilized reagents and protects them from oxidation and degas driven loading still remains fully functional.

According to another aspect of the presently disclosed technology, the DS chip may be designed to be disposable with no outlets; therefore biohazard contamination risk can be minimized.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

The presently disclosed technology makes it possible to bypass costly and multistep sample analysis assays and provides a low cost point-of-care solution for quantitative sample analysis. For example, the Digital Separation (DS) technology can be used to detect HIV viral load in whole blood. It is possible to perform HIV-1 RNA detection in ~40 minutes directly from whole blood samples. Since only an endpoint readout is needed, a fluorescent microscope or smartphone with simple filters can be used for detection. Throughput is also large since multiple assays can be run in parallel as real time monitoring is not necessary. The disposable system may be completely passive and no external power sources or pumps are required. This is a significant improvement compared to, for example, current real-time PCR systems with regard to the steps needed, assay time, and cost.

The disclosed apparatus and methods provide parallel fluid sample preparation and quantitative sample analysis in a single step, designed to be fast, inexpensive, portable and simple to use. To enable one-step quantitative sample analysis, two sample preparation functions can be integrated on a fluidic chip: suspension separation and sample digitization.

Suspension separation (e.g. separation of plasma and blood cells in whole blood) can be essential for both protein detection and nucleic acid assays. For example, the hemoglobin in red blood cells can obscure optical readouts because of its opaqueness. Hemoglobin is also a well-known NA amplification inhibitor as the chelating properties disrupt the ion concentrations in the sample and thus inhibit polymerase activity.

Sample digitization for sample analysis allows quantitative digital detection of NA template concentration, protein concentration, antibody concentration, metabolite detection, etc. The data acquired using the presently disclosed apparatus and methods are comparable to that which a costly thermal cycler, microplate spectrophotometer or other complex reader could provide. However, the presently disclosed apparatus and methods cost only a few dollars to construct and perform.

One example assay that may be integrated with the DS chip is digital nucleic acid detection. The working principle of digital nucleic acid detection is to dilute the template concentration low enough so that each well has either a few or zero NA copies, and then perform an amplification step. By reading the endpoint result, it is possible to count the number of positive wells fluorescing, yielding the template concentration data without the need for Ct values as would be used in real time NA amplification methods. A simple fluorescence and an endpoint count of positive wells can be done by a smartphone with filters.

Figure 1A:
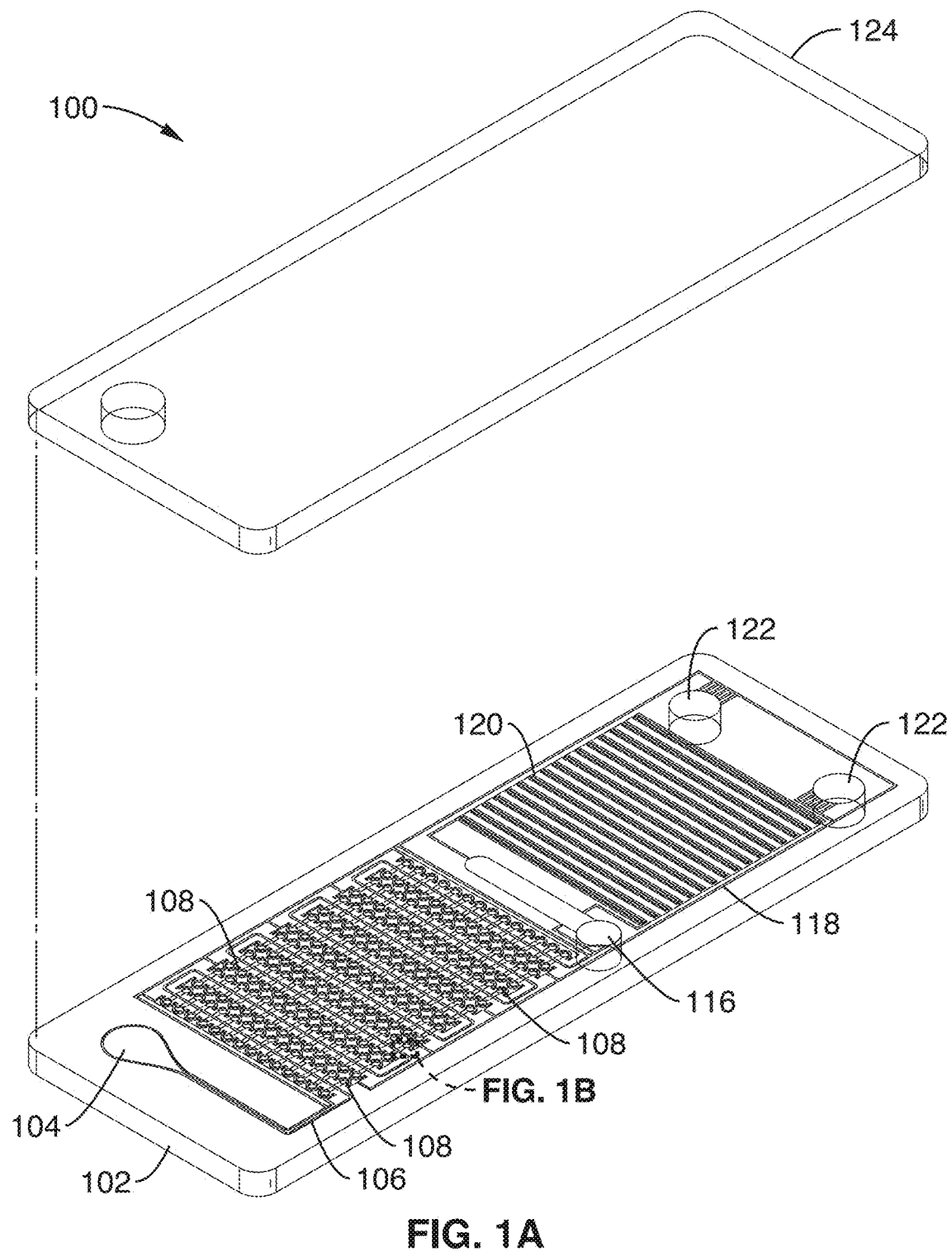
FIG. 1A is schematic diagram of a two layer design embodiment of the Digital Separation (DS) chip.

Referring now to FIG. 1A, a schematic diagram of an embodiment of the Digital Separation (DS) chip 100 is presented. In this embodiment, a simple two layer chip design is shown that is intended for easy mass fabrication by injection molding with a thermal elastomer gas permeable material, such as PDMS. Fabrication of the chip is straightforward and adoptable for scalable production; a simple two layer mold can be used (with feature sizes of 30 to 400 μm) for injection molding/hot embossing. The DS chip 100 preferably has a top cover layer 124 and a bottom fluidic layer 102. The bottom fluidic layer 102 of the DS chip 100 includes a sample inlet 104 that receives the sample. Once the sample has been loaded onto the chip, it flows through a channel 106 that is lined by wells 108. The user can simply drop the sample onto the chip and sample flow starts automatically using degas driven flow, in this example. Degas driven flow can be used where acquiring electricity is not feasible. Degas driven flow operates by utilizing the inherently high porosity and air solubility of gas permeable materials such as PDMS by removing air molecules from the material (PDMS) and initiating flow. Although in this embodiment there is no need for external power sources for fluid flow, it should be understood that in other embodiments, an external source may be used to move fluid within the chip.

In this embodiment, the wells 108 are perpendicular to the channel 106. Cliff structures 110 (see FIG. 1B), which are perpendicular to the channel 106 and adjacent to the wells 108, may be used to separate solution from particles in cases where the sample is a suspension (e.g. whole blood). The mechanism of suspension skimming is based on gravity induced sedimentation. The channel 106 may be configured in a serpentine shape on the chip and may connect to an array of side skimming cliff structures, allowing for large arrays (>200) of suspension to be separated in ~10 minutes.

Figure 1B:
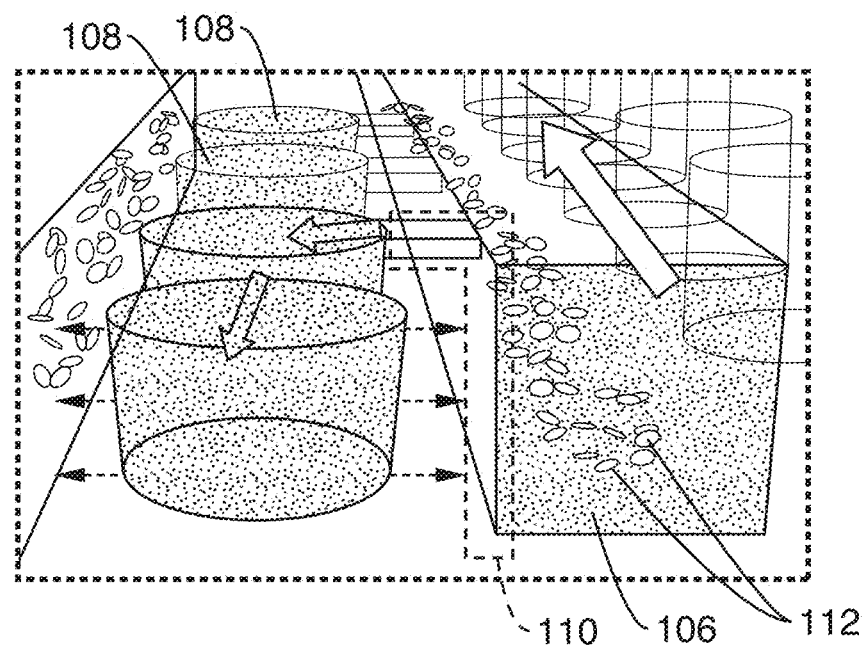
FIG. 1B is a zoomed in view of a cliff structure according to an embodiment of the present disclosure.

Turning now to FIG. 1B, a close up perspective view of an embodiment of the cliff structure 110 is shown. As the sample flows through the channel, particles 112 (e.g. blood cells), in the suspension fall to the bottom of the channel 106 and are unable to move over the cliff structure 110. The solution portion is able to flow over the cliff structures 110 and into the wells 108. The arrows show the direction of the degassing fluid flow.

Figure 2A:
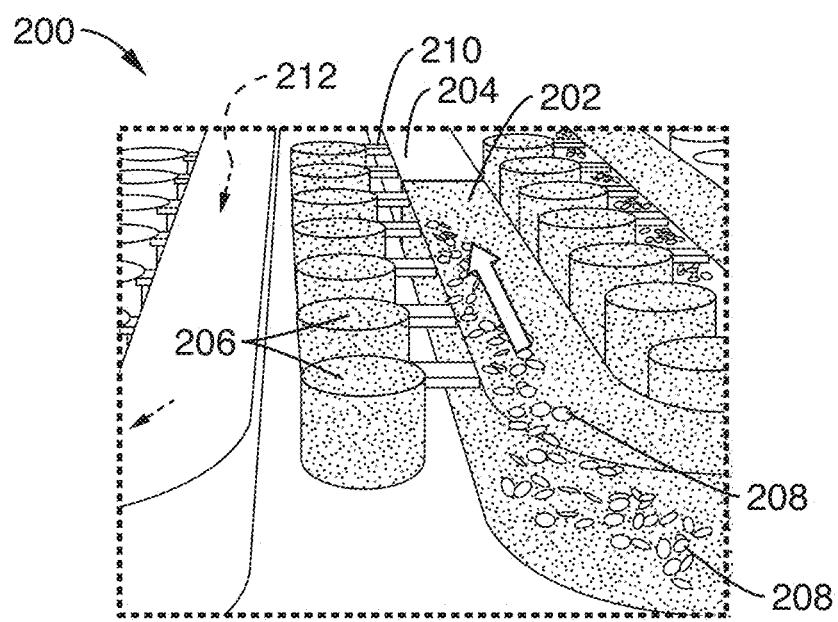
FIG. 2A, FIG. 2B and FIG. 2C are schematic diagrams of a perspective view of a sample fluid flowing through the DS chip.
Figure 2B:
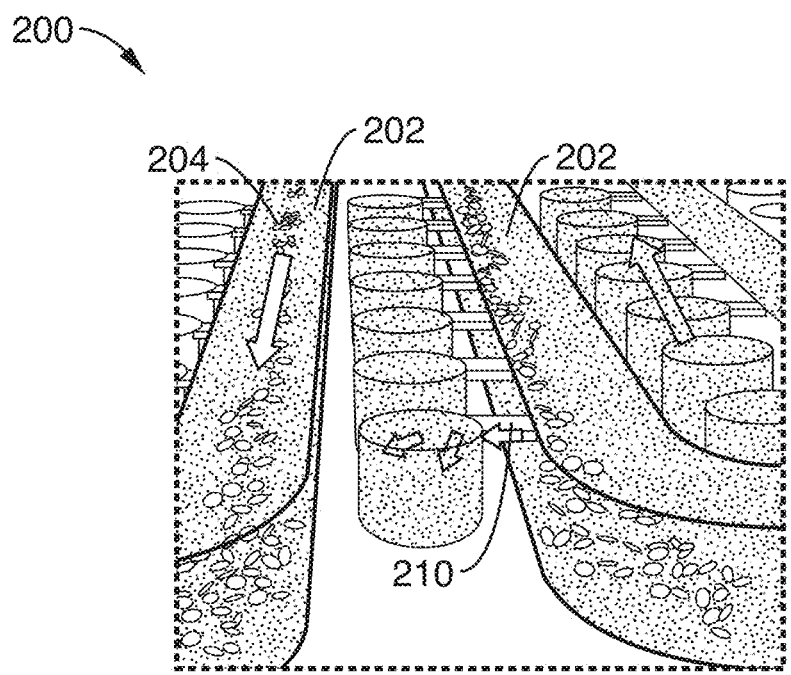
Figure 2C:
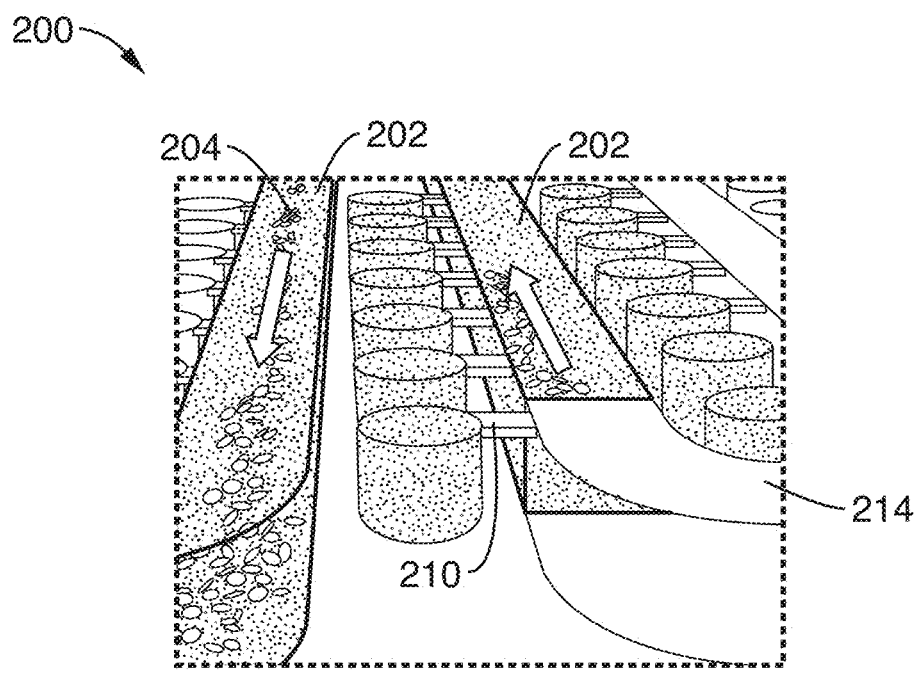

FIG. 2A, FIG. 2B and FIG. 2C show schematic diagrams 200 of close-up side views of a sample fluid flowing through the DS chip. FIG. 2A shows the sample 202 begin to flow through the filled channel 204 and into the wells 206 by degas driven flow. The arrows indicate the direction of fluid flow and show the solution moving into the wells 206 while most particles 208 are left at the bottom of the channel due to sedimentation. The particles 208 are unable to move over the cliff structures 210, which thereby purify the sample. The empty channel 212 degassing air is shown ahead of the sample fluid. As shown in FIG. 2B and FIG. 2C, once the solution has been loaded into the wells, the solution can be compartmentalized by an air plug 214. Thus, the solution can be sealed in the wells without the need for an oil phase. In one step, the sample can be purified and digitized and ready for NA amplification.

Figure 3A:
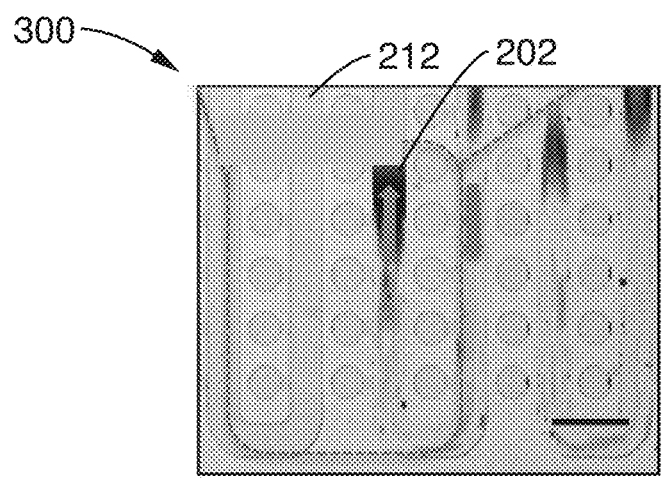
FIG. 3A, FIG. 3B and FIG. 3C are top view images of the schematic diagrams shown in FIG. 2A, FIG. 2B and FIG. 2C.
Figure 3B:
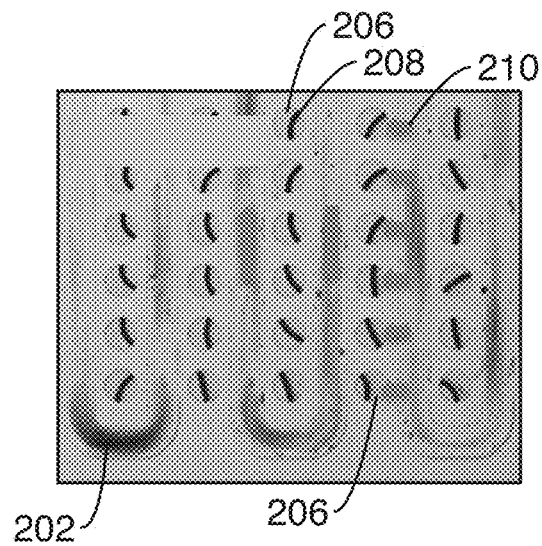
Figure 3C:
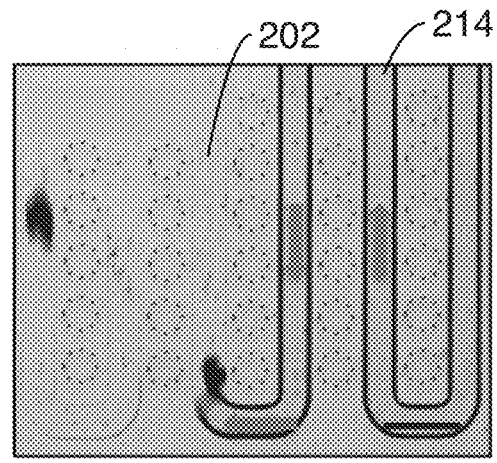

FIG. 3A, FIG. 3B and FIG. 3C are top view images 300 of the schematic diagrams shown in FIG. 2A, FIG. 2B and FIG. 2C.

NA amplification may be achieved by premixing the sample with NA amplification reagents, where an amplification initiating reagent may be patterned onto the surface of the wells before addition of the sample. When the sample plus NA amplification reagents flow into the well and contact the final reagent, NA amplification is initiated.

Protein analysis may be achieved by running a sandwich ELISA in the wells. Capture antibody/aptamers can be pre-printed in the well area, and fluid samples can be mixed with primary and secondary antibodies prior to being loaded into the sample inlet. The micro-cliff structure can separate the blood cells while retaining the protein biomarkers. Once the antigen proteins are captured in the wells by the pre-printed antibody/aptamers, the signal can be amplified via a fluorescence probe or standard chemi-luminesce or color change reaction (e.g. horse radish peroxidase oxidation) and an endpoint readout taken.

Analysis of many other components in a fluid sample may also be achieved, including but not limited to, antibodies, amino acids, peptides, sugars and fats.

Turning back to FIG. 1A, the DS chip 100 may also be equipped with a single large well 116 (>65 μl in a microfluidic chip for example) for trench based suspension separation and qualitative readout for lower concentration samples (for example, $10^2$-$10^4$ copies/ml in the case of NA detection). Additionally, degas proximal lines 118 may be added to the chip for vacuum loading. Auxiliary degas proximal lines 120 may also be added to help increase the speed of fluid loading. The DS chip may also include large vacuum capacitor chambers 122 to retain vacuum suction for at least an hour. The fluidic layer 102 may be covered by a blank layer 124 of material, which may be a gas permeable material to enhance degas loading.

The presently disclosed technology may be better understood with reference to the accompanying examples, which are intended for purposes of illustration only and should not be construed as in any sense limiting the scope of the presently disclosed technology as defined by the claims appended hereto.

EXAMPLE 1

As an example of blood based disease NA detection, HIV viral load quantification in blood was used as a demonstration. To demonstrate digital NA amplification, Recombinase Polymerase Amplification (RPA) was used, which is a ~40° C. isothermal NA amplification technique. With 30 minutes of incubating at 40° C. using reusable instant heat packs, on-chip detection of HIV-1 RNA from spiked blood samples was achieved. The quantitative digital nucleic acid (NA) detection dynamic range was $10^3$-$10^6$ copies/ml.

RPA was chosen because of the relatively low incubation temperature that is required. The lower incubation temperature greatly reduces the risk of generating air bubbles, in contrast to using PCR, which heats the samples up to 95° C. RPA is also the fastest isothermal amplification method commercially available to date. This, in combination with its robustness when used with plasma samples, made it an ideal NA amplification technique to integrate with the DS chip. It should be appreciated, however, that the DS chip is designed to be compatible with other isothermal techniques (e.g. helicase-dependent amplification (HDA), strand displacement amplification (SDA), nucleic acid sequence-based amplification (NASBA), and signal-mediated amplification of RNA technology (SMART)) as well as other NA assays, protein detection assays, immuno-assays, etc. Using RPA, sample preparation, sample digitation (compartmentalization) and NA amplification were all integrated without the need for an oil phase.

Figure 4:
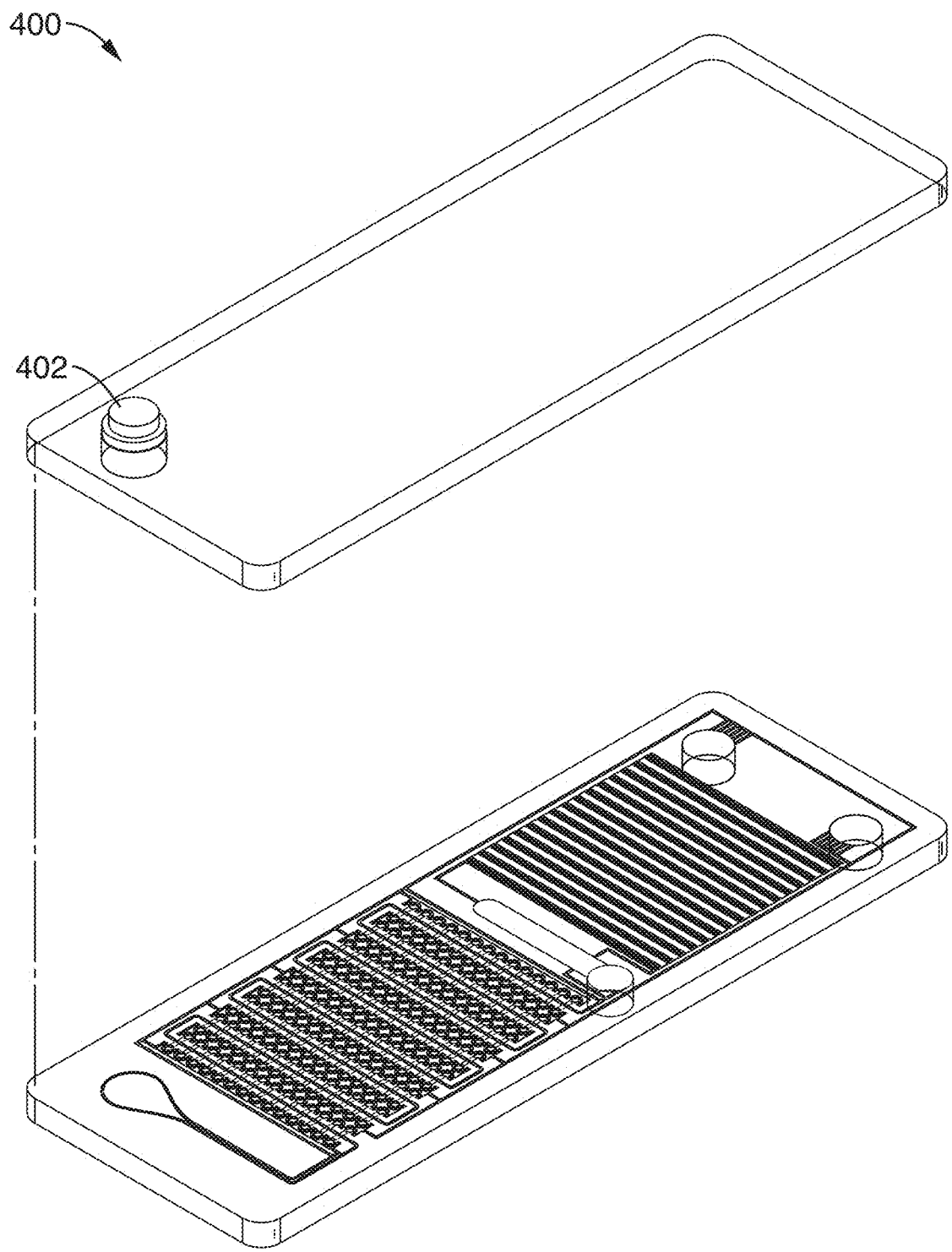
FIG. 4 is a schematic diagram of the DS chip with a thumb-pump, according to an embodiment of the present disclosure.
Figure 5A:
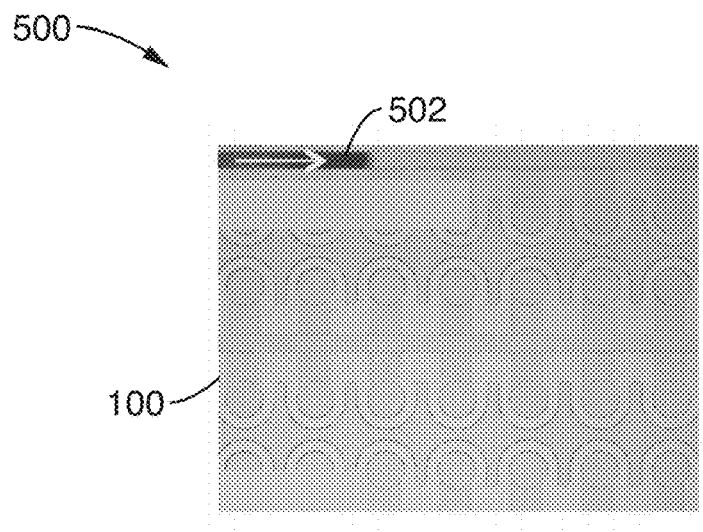
FIG. 5A through FIG. 5F are time lapse images of a digital plasma separation in the DS chip, according to an embodiment of the present disclosure.
Figure 5B:
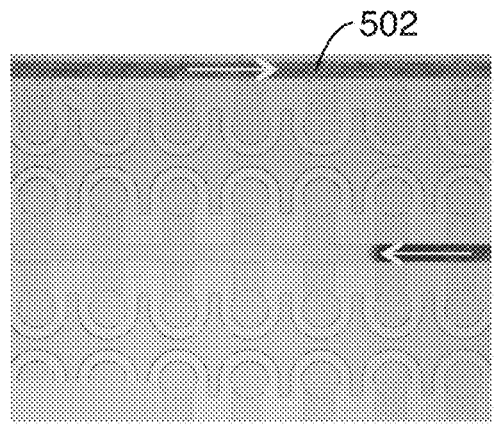
Figure 5C:
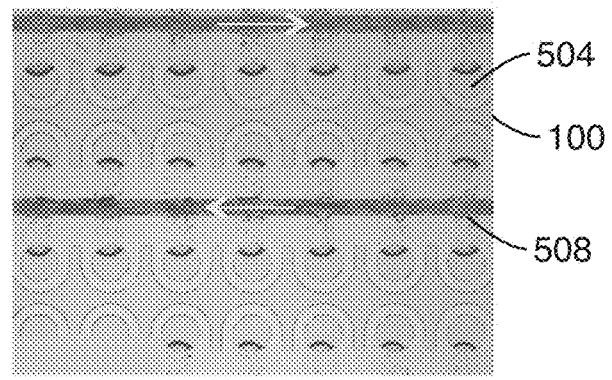
Figure 5D:
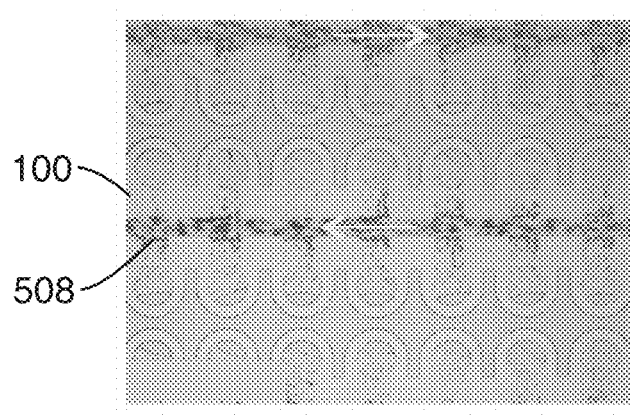
Figure 5E:
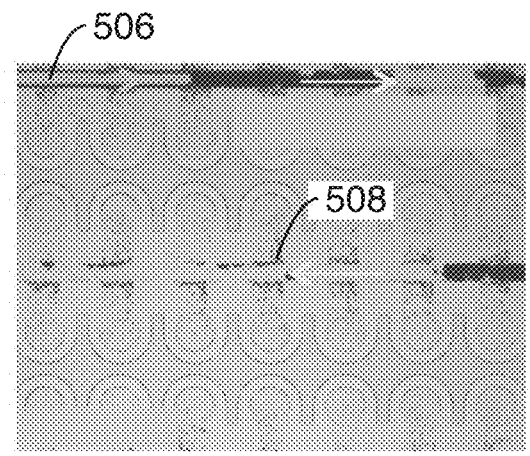
Figure 5F:
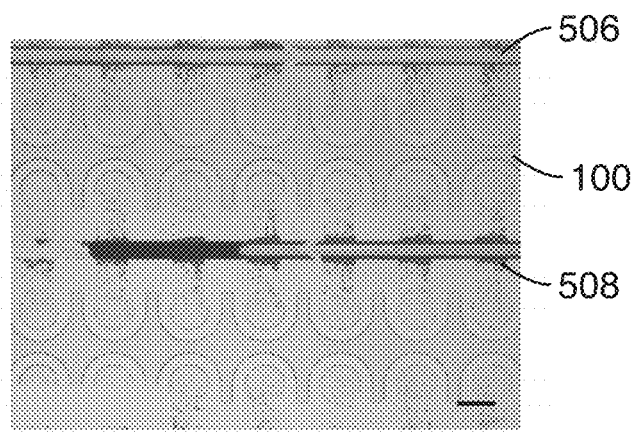

In this illustration, chip cliff structures were used to skim the top part of plasma from a blood sample mixed with RPA reagents. All sample loading was actuated by degas driven flow; therefore, no external pumps were required. It was observed that the DS chips may be stored in vacuum food aluminum packaging (Van Der Stahl Scientific, V402), and are fully functional for up to at least a year. It was also observed that RPA reagents induced blood cell coagulation, which enhanced the separation effect as sedimentation speed is increased. However, there was no clogging and no lysing observed. The main serpentine loading channel was connected to an array of side skimming structures, allowing large arrays (>200) of plasma skimming in ~10 minutes. It was also demonstrated that the DS chip could be integrated with thumb-pump microSIP flow, as shown in FIG. 4. In this embodiment 400, no initial degassing is required and the user can actuate fluid flow by simply using a thumb press 402.

The skimming channel was constructed 40 μm deep and the main loading channel 300 μm deep. Digitization happened automatically when the blood sample finished loading. An air plug passed through to compartmentalize each well. RPA reactions were initiated in each well using MgOAc patterned within the wells. A reusable commercial Sodium Acetate instant heat pack provided heating at ~40° C. for up to an hour for isothermal amplification. An endpoint fluorescence image was taken using a microscope (Axiozoom, Zeiss). Based on Poisson statistics, the original template concentration was back calculated by counting the percentage of fluorescing wells.

All HIV RNA detection experiments were done with the RPA RT-exo kit (Twistdx, UK). 10 μl of human whole blood (HMWBACD, Bioreclaimation) was mixed with a RPA mix (10 μl of primer/probe mix, 40 μl of rehydration buffer, 2 μl of 10% BSA, 8 μl of RNAsin, and 10 μl of spiked HIV RNA). 100 μl of blood/RPA mix was added into each chip and incubated at 40° C. Endpoint fluorescent images were taken (FAM channel) with an Axiozoom macroscope (Zeiss). HIV RNA was HIV-1 subtype B (Seracare, 500405). HIV specific primers and probes were supplied from Twistdx collaborators. RNAsin was bought from Promega (N2611).

The fluidic layer of the chip was fabricated with standard soft lithography in PDMS. This platform can be easily integrated with other soft lithography based microfluidic technologies. Since the construction is based on standard silicon (PDMS) molding, other components such as CD4+T cell counting, protein detection, optical components, mixers, diluters, valves, diodes, electrodes, can be easily integrated as the fabrication processes are highly similar.

The fluidic layer was covered by another blank PDMS substrate to enhance degas loading. On the top and bottom of the chip, glass cover slips were used to provide a barrier to air diffusion, which prolongs the degas loading and also provides mechanical stability. Since the construction of the chip is simple, it can be adopted easily for injection molding/hot embossing to scale up production. MgOAc, the reagent that initiates RPA reaction, was patterned by degas drying onto the chip. The chip was designed with 200 wells, each well having a height of 300 μm and a diameter of 650 μm, which gives a total volume of 100 nl. This is designed to give a dynamic range of detecting $10^3$ to $10^6$ copies/ml, which corresponds to the clinical concentration of HIV RNA in clinical samples. Although the system would saturate beyond $10^6$ copies/ml, it still provides a clear indicator that viral load is extremely high and the patient is in a very serious disease state. A large single chamber (80 μl, for example), which can detect extremely low RNA copy samples of ~$10^2$ copies/ml, was also included in this example embodiment (see FIG. 1A) for qualitative, yes/no assays. This can be a beneficial feature because it makes the chip able to catch early infection in patients who do not have a high viral titer yet. The dynamic range can also be further tuned by simply modifying the well sizes and number.

Referring now to FIG. 5A through FIG. 5F, time lapse images 500 of digital plasma separation are sequentially shown. In this example, human whole blood 502 was mixed with RPA reagents and loaded onto a DS chip 100 (see FIG. 1A). Plasma 504 was skimmed into two-hundred wells and compartmentalized in one step with an air plug 506. The red blood cells 508 can be seen as black debris. The arrows indicate the direction of flow.

Figure 6A:
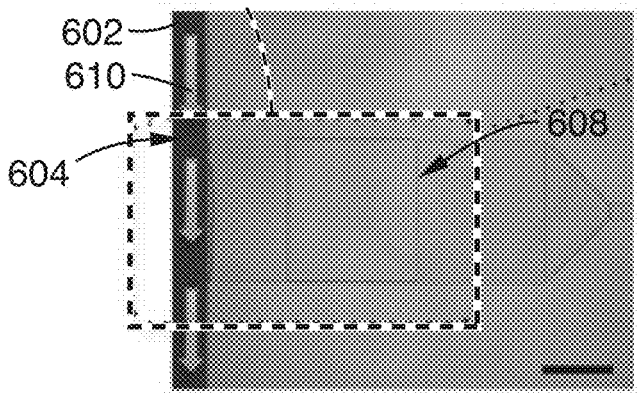
FIG. 6A through FIG. 6D are time lapse images of a blood sample moving through the channel and across the cliff structure.

FIG. 6A through FIG. 6D are close-up time lapse images 600 of the blood sample 602 moving through the channel 604, across the cliff structure 606 (see FIG. 6E) and into the small gap cliff structure 608. The arrows 610 represent the direction of flow. FIG. 6A shows t=0 seconds as the blood sample 602 is loaded into the channel 604. In this embodiment, shown in a close-up view schematic diagram in FIG. 6E, an auxiliary micro-trench 612 was also included, which helps to increase the speed of separation of the plasma 614 and blood cells 616. However, the cliff structure 606 can function to separate the sample on its own.

Figure 6B:
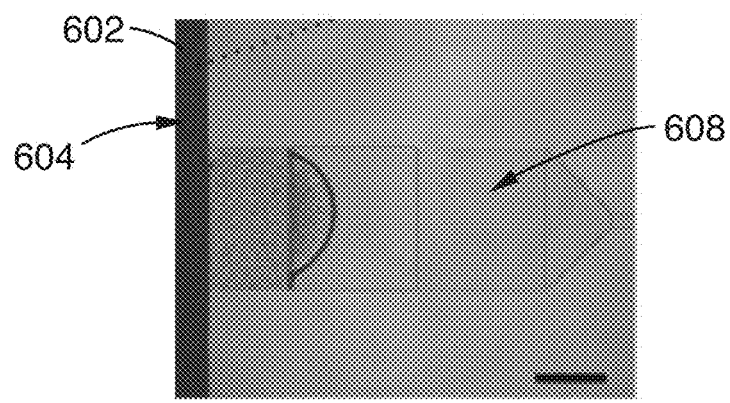
Figure 6C:
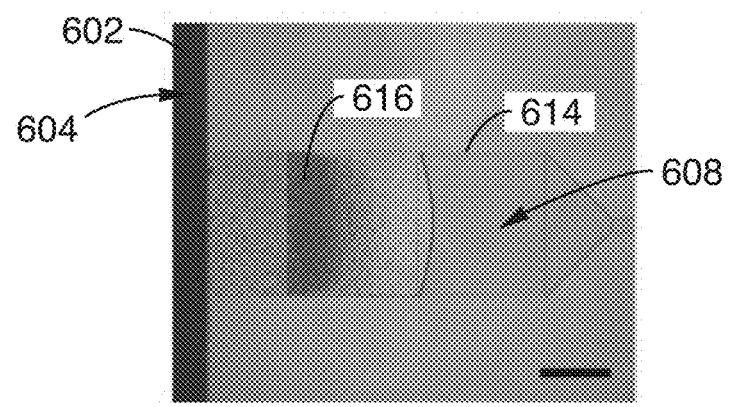
Figure 6D:
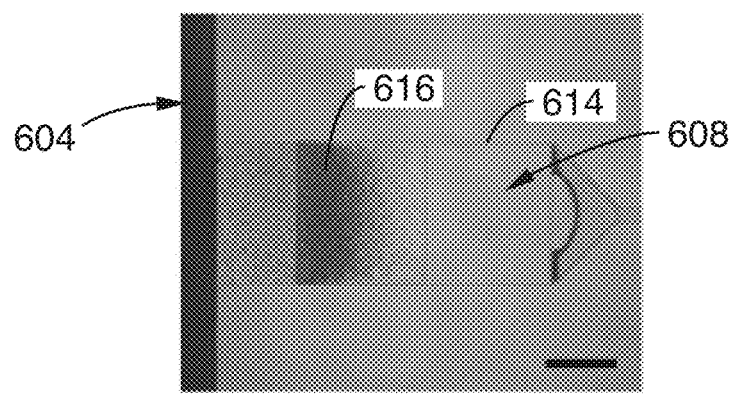
Figure 6E:
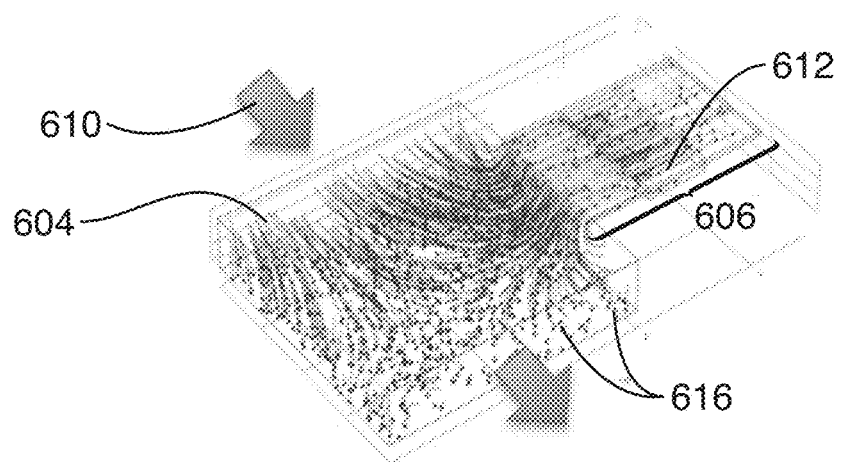
FIG. 6E is a schematic diagram of blood flowing over a cliff structure.

FIG. 6B shows t=35 seconds where the blood sample 602 has entered the auxiliary micro-trench 612. At t=85 seconds, shown in FIG. 6C, the plasma 614 and blood cells 616 begin separating. In FIG. 6D, the plasma 614 enters the well (not shown) while the blood cells 616 remain outside of the well. The skimmed plasma can enable RPA fluorescence readout to be detected.

Figure 7:
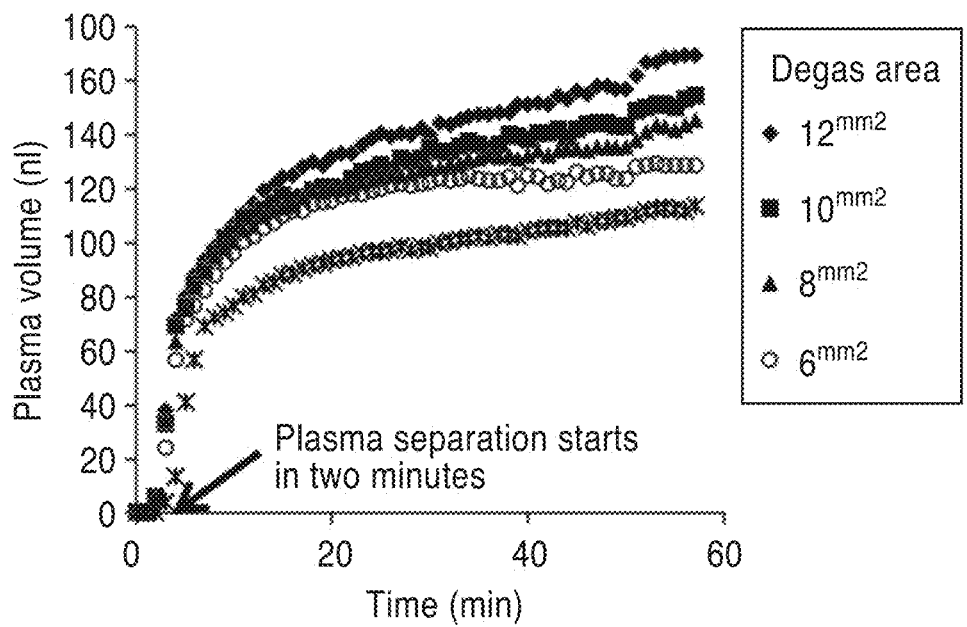
FIG. 7 is a graph illustrating that plasma separation was shown to be initiated within two minutes and separated plasma volume and speed could be tuned by changing the degas surface area of the cliff structure and well.
Figure 8:
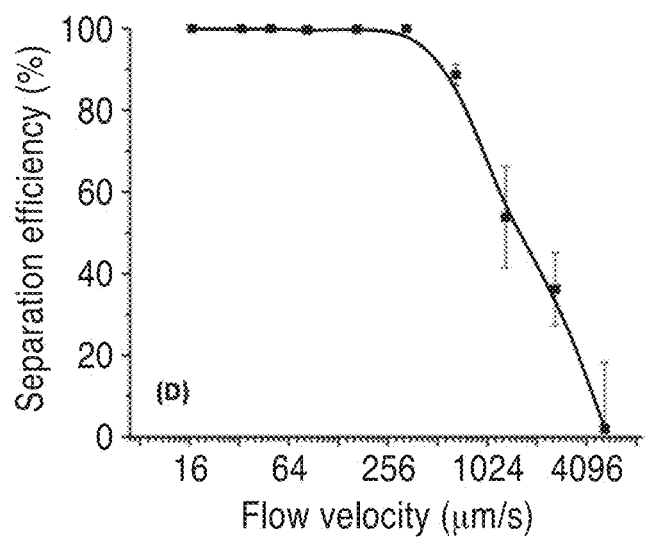
FIG. 8 is a graph showing plasma separation efficiency.

FIG. 7 shows a graph of plasma separation times. Separation was shown to be initiated within two minutes and separated plasma volume and speed could be tuned by simply changing the degas surface area of the side cliff structures and wells. FIG. 8 is a graph showing plasma separation efficiency. The plasma separation efficiency was >98% when flow velocities were below a threshold of $2 \times 10^3$ μm/s. As long as flow rates did not exceed the maximum threshold, plasma skimming remained robust.

Figure 9A:
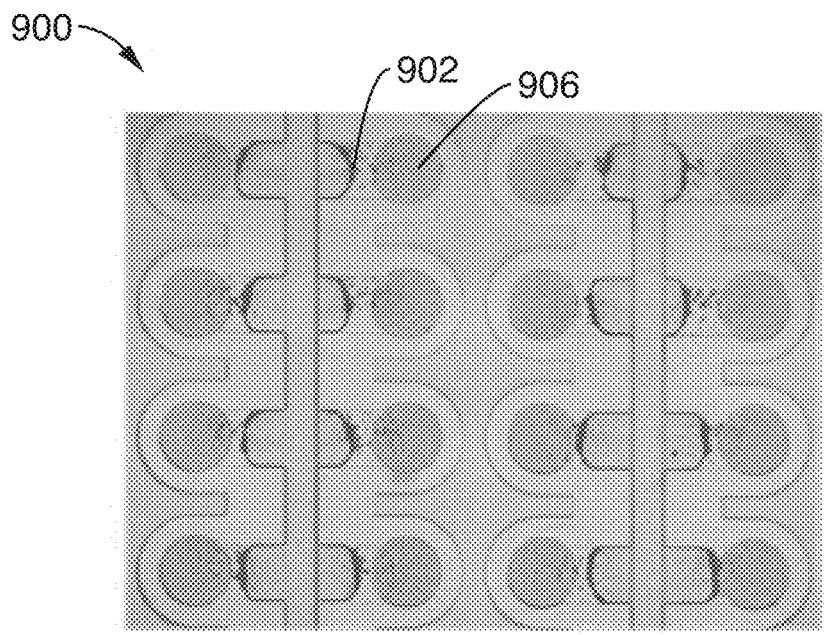
FIG. 9A and FIG. 9B show images of blood sample compartmentalization with and without cliff structures, respectively.
Figure 9B:
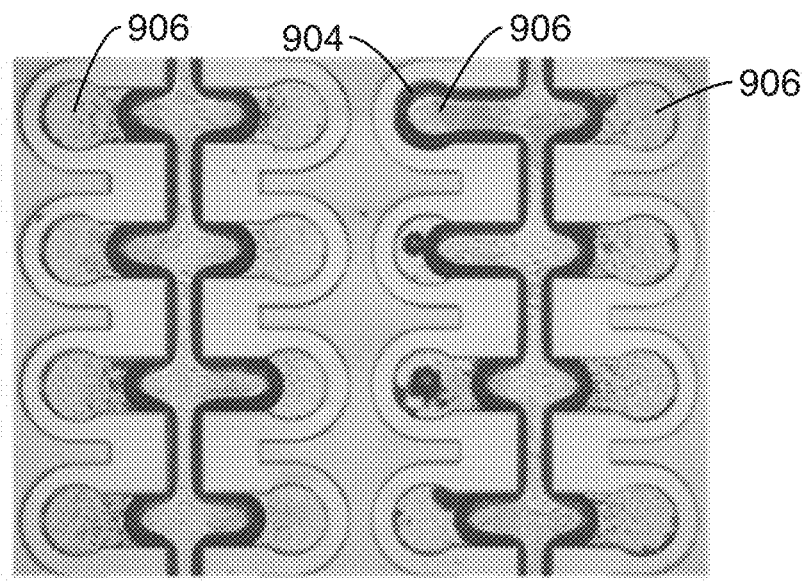

It was verified that the cliff structures helped to maintain uniformity of separation volume and remove the red blood cells that can interfere with NA amplification and fluorescence readout. FIG. 9A and FIG. 9B show images 900 of blood sample compartmentalization with and without cliff structures, respectively. FIG. 9A shows how the cliff structures 902 help plasma separation and enable consistent volume loading. FIG. 9B shows that without the cliff structure, aggregates of red blood cells 904 migrate into the wells 906, which can interfere with the fluorescence readout. The loaded liquid volume is also much less consistent. Each well is 650 μm in diameter. Human whole blood was mixed with RPA reagents and then loaded into the DS chip.

Very large numbers of wells (10 to 1500 wells, 30 to 100 nl/well) were separated in ~10 minutes. A 50 to 100 μl blood sample can be processed within 10 minutes, yielding digitized plasma compartments with 20 to 50 μl. The volume of separated plasma can be easily tuned by adjusting the number and size of wells.

Figure 10:
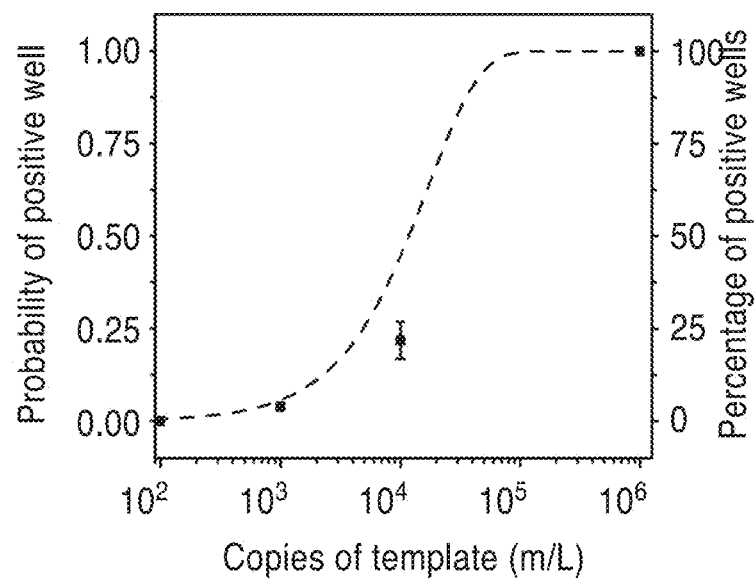
FIG. 10 is a graph of the results of digital amplification of different template concentrations with on-chip RPA.

FIG. 10 shows the results of digital amplification of different template concentrations with on-chip RPA. A detection limit of ~$10^3$ copies/ml and a dynamic range of $10^3$ to $10^6$ copies/ml were achieved. Here, positive control MRSA DNA was diluted in water and loaded onto the DS chip and digitized in one-step. The line shows the theoretical prediction based on Poisson statistics and the dots represent experimental data, n=4.

Figure 11A:
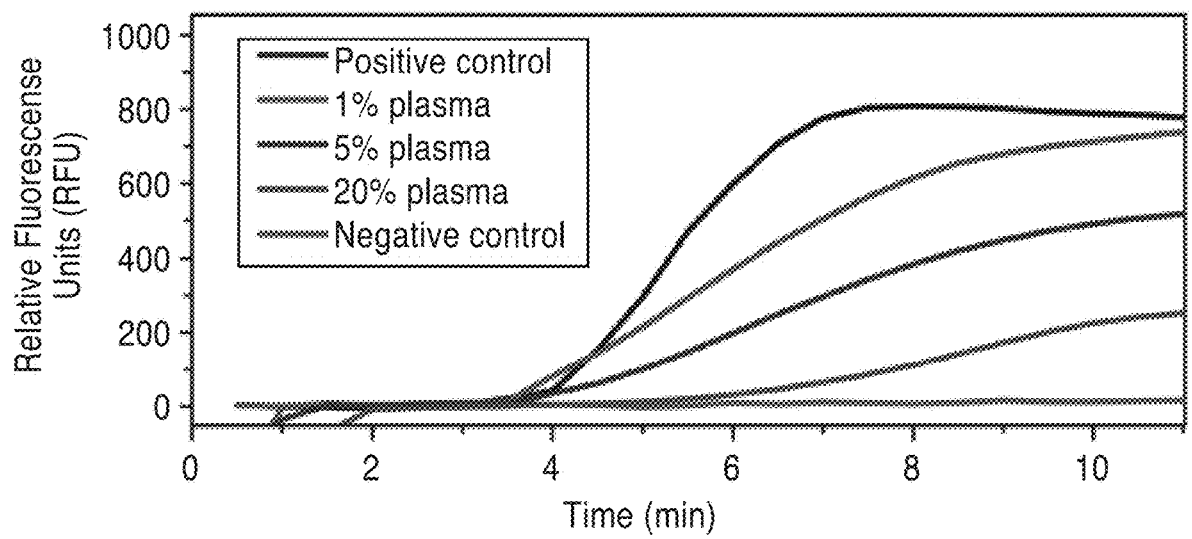
FIG. 11A and FIG. 11B are graphs illustrating how plasma separation and dilution are necessary for RPA reactions.
Figure 11B:
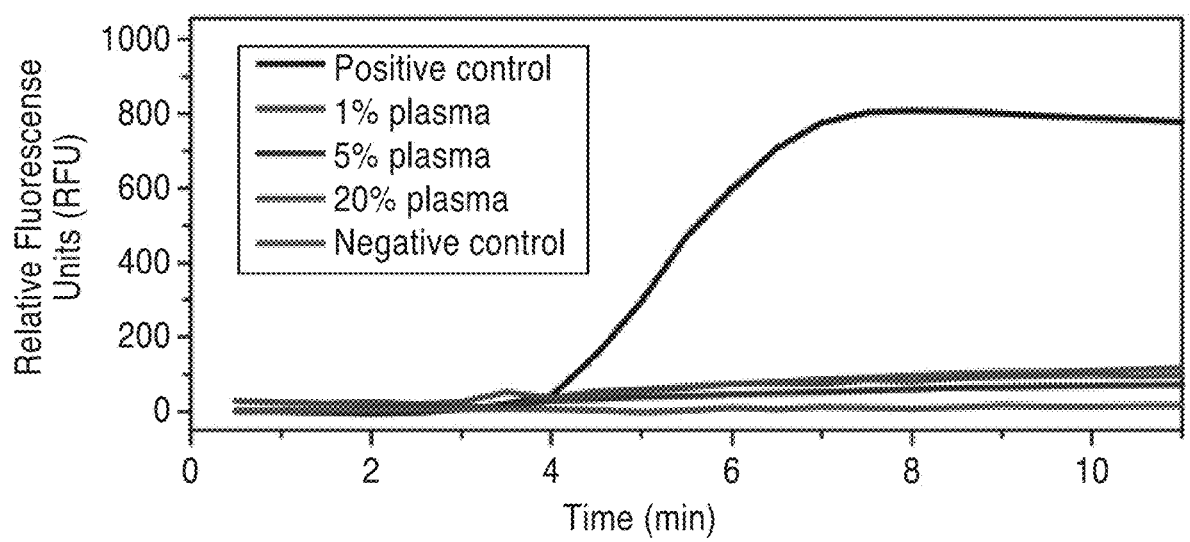

FIG. 11A and FIG. 11B illustrate how plasma separation and dilution are necessary for RPA reactions. Newer plasma resistance polymerases (e.g., Thermo Scientific—Phusion) have shown direct amplification from 40% whole blood; however, only endpoint gel electrophoresis assays can be performed as the opaque red blood cells need to be removed so that they do not obstruct optical fluorescence readout. Isothermal assays such as RPA showed amplification in up to 20% plasma. With the newer plasma resistant assays, it is possible to amplify directly from plasma samples, but red blood cells still needs to be removed for clear optical detection. Therefore, plasma separation methods for rapid NA detection were developed. For this assay, off-chip RPA was performed with different dilutions of plasma, shown in FIG. 11A, and whole blood, shown in FIG. 11B. The results indicate that RPA can function in up to 20% (total reaction volume) of plasma and detection can happen within 10 minutes (100 copies/ml). RPA does not produce a signal in whole blood. It was concluded that RPA is a more robust downstream NA assay compared to LAMP and PCR, which fail at ~1% plasma/blood. This result guided the design of sample preparation modules geared towards plasma separation. Positive controls were DNA templates in pure water.

Figure 12:
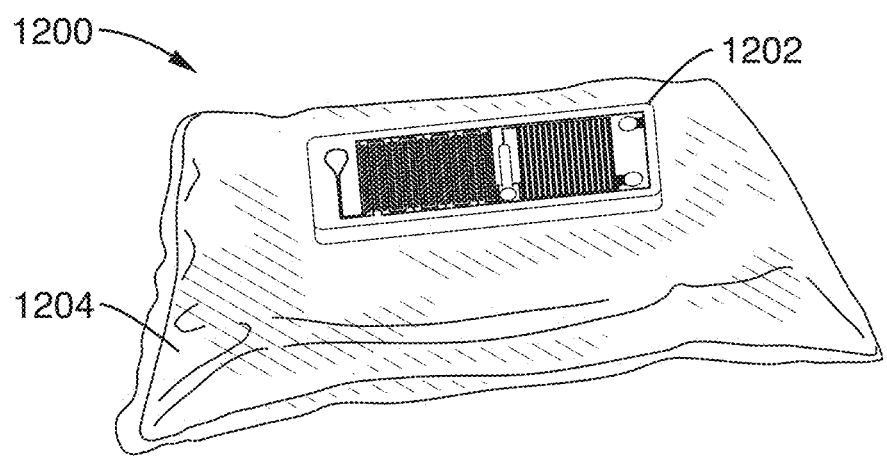
FIG. 12 is a diagram of a DS chip disposed on a heat pack according to one embodiment of the disclosure.
Figure 13:
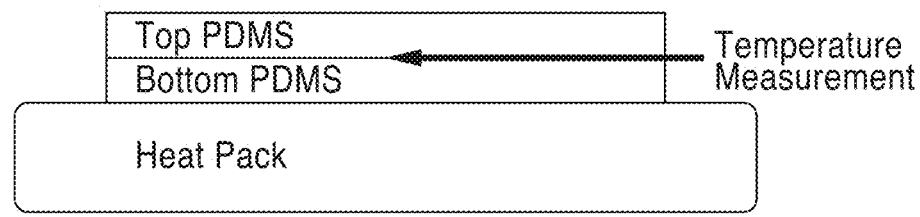
FIG. 13 is a schematic diagram showing where the temperature measurements were taken during heating of the DS chip on a sodium acetate heat pack.

The chip's thickness was optimized to 2.9 mm for both top and bottom PDMS layers so an instant sodium acetate heat pack could provide instant heating at ~40° C. for up to an hour. FIG. 12 is a schematic diagram 1200 of the DS chip 1202 resting on the heat pack 1204. A commercial reusable instant heat pack (Hotsnapz) was used. This sodium acetate heat pack can be reused after immersing in boiling water and costs less than $2. FIG. 13 shows a schematic diagram of where the temperature measurements were taken, in between the PDMS layers.

Figure 14:
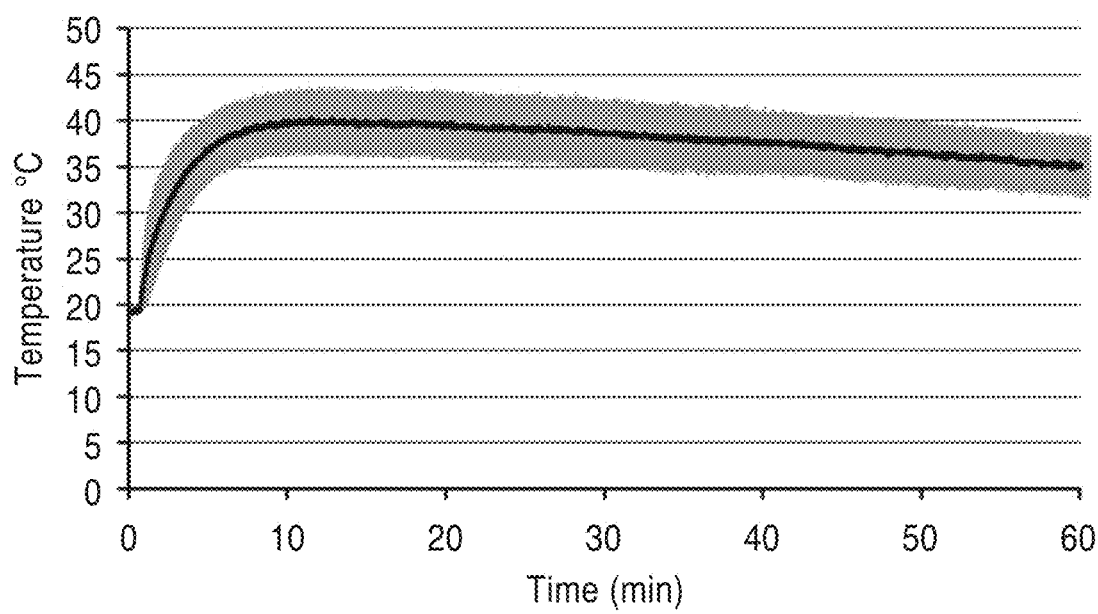
FIG. 14 is a graph showing the temperature measurements over time during heating of the DS chip.

FIG. 14 is a graph showing the temperature measurements over time, where n=3, during heating of the DS chip for NA amplification. Digital amplification reactions were run by simply placing the DS chip onto the heat pack for 20-60 minutes as shown in FIG. 12. This method was shown to be compatible with various isothermal NA amplification technologies, such as NASBA, SMART, SDA, BAD and AMP. It should be noted that NA amplification can proceed at room temperature but takes longer to complete.

Figure 15:
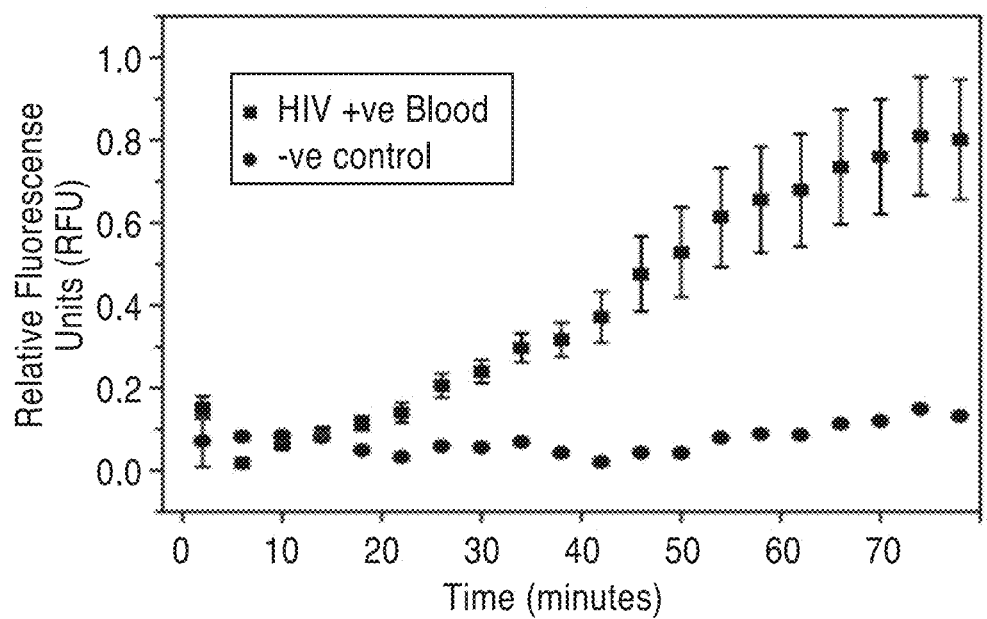
FIG. 15 is a graph of fluorescence over time for a one-step, 30 minute HIV NA in a whole blood detection assay.
Figure 16A:
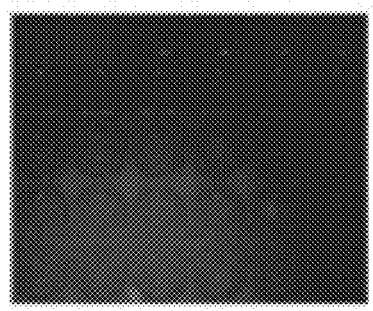
FIG. 16A is an image of fluorescence on the DS chip at 0 minutes.
Figure 16B:
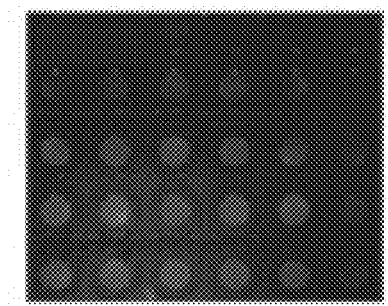
FIG. 16B is an image of fluorescence on the DS chip at 30 minutes and FIG. 16C is an image of fluorescence on the DS chip at 60 minutes.
Figure 16C:
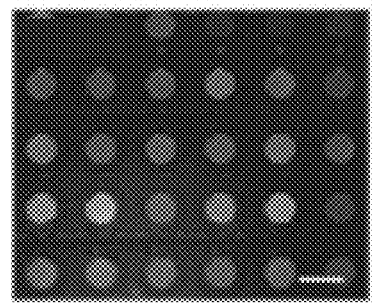

FIG. 15 through FIG. 16C show the capability (results) of sample loading, separating plasma, digitizing the samples and RPA detection of HIV RNA templates in one-step within 30 minutes at 40° C. using HIV genomic RNA spiked whole blood at $10^6$ copies/ml. FIG. 15 is a graph showing fluorescence over time. FIG. 16A is an image of fluorescence on the DS chip at 0 minutes, FIG. 16B is an image of fluorescence on the DS chip at 30 minutes and FIG. 16C is an image of fluorescence on the DS chip at 60 minutes. These results show that it is possible to perform quantitative endpoint NA assays without a thermal cycler in 30 minutes. Since only an endpoint fluorescence image is needed, it is possible to use simple optical filters and a smartphone to obtain an image. Using a smartphone to perform HIV viral load assays with the DS chip can provide inexpensive nucleic acid based quantitative telemedicine.

These results indicate that it is possible to perform on-chip HIV RNA detection from whole blood in less than 40 minutes using the DS chip, in one step. This is much faster and requires less manual operation compared to current commercially available systems (e.g. Spin column+RT-PCR) for quantitative NA testing.

EXAMPLE 2

This assay was performed to demonstrate that digital separation can integrate sample preparation with digital isothermal amplification using RPA, to detect Methicillin-resistant *Staphylococcus aureus* (MRSA) DNA directly from human whole blood samples in 30 minutes.

Using the cliff structures described in FIG. 1B, blood cell sedimentation was also used in this example to skim plasma into the wells. By separating the red blood cells, there is less optical obstruction of the fluorescence signal and less enzymatic interference of the polymerase due to hemoglobin inhibition. Since there is very low shear stress created on the red blood cells, there is minimal hemolysis. The DS chip design also avoids blood cells clogging since there are no features that would cause blood cell stacking against the flow. DS enables digital NA amplification assays (e.g. RPA) to be performed directly from separated plasma or other sample. In this example, the cliff structures and wells were arranged in an array so that large numbers (200 to 1500) of wells could be processed in parallel. These samples were also compartmentalized by an air plug automatically and fluid flow was performed by degas driven flow. RPA reactions were utilized in each well to commence digital NA amplification.

Microfluidic chips were fabricated with the standard soft lithography processes. PDMS was cast onto SU8 patterned wafers. Blood and RPA reagents were mixed prior to loading. 100 µl of blood samples mixed with RPA reagents (RPA exo kit, Twistdx) were loaded each time. Partial components of the RPA mix were lyophilized into the wells. The DS chips were stored in a vacuum (−70 kPa) overnight before loading samples. Samples may be sealed in vacuum pouches and may still be fully functional for up to a year at least. After the samples were loaded and compartmentalized, the chip was put in a 37° C. incubator for RPA incubation. After incubation, fluorescence signal was detected by a fluorescence microscope (Zeiss, Axiozoom).

Figure 17:
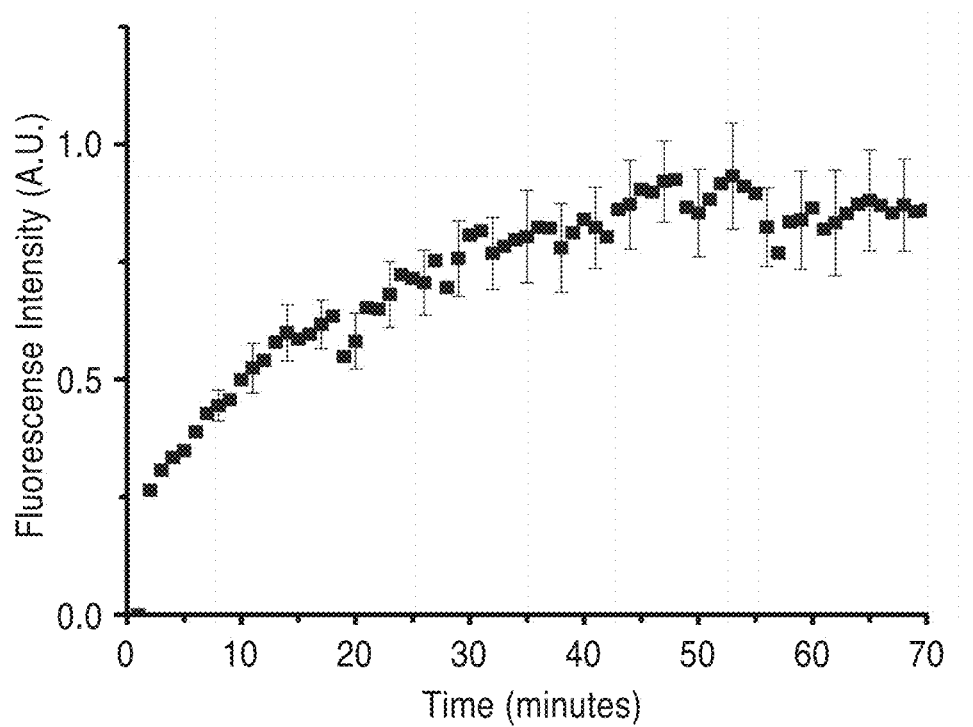
FIG. 17 is a graph of the detection of the MRSA Mec A gene DNA added to whole blood at $10^6$ copies/ml and mixed with RPA reagents.
Figure 18A:
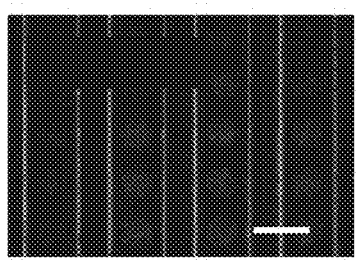
FIG. 18A, FIG. 18B and FIG. 18C are fluorescence images taken (FAM channel) with a stereoscope at t=0 minutes, t=20 minutes and t=50 minutes, respectively.
Figure 18B:
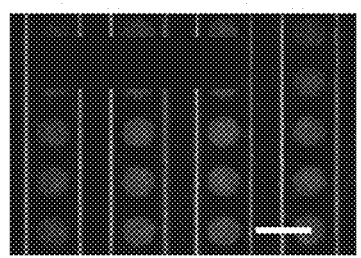
Figure 18C:
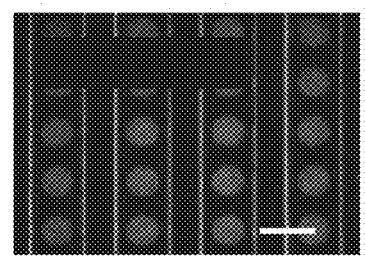

Plasma separation efficiency was >99% when flow rates into the wells were lower than 100 µm/s. One-step plasma separation and sample compartmentalization was possible in ~10 minutes. About 200-1500 wells of plasma (30 to 100 nl/well) can be separated from whole blood mixed with RPA reagents (100 µl). The user can drop the blood/RPA mix onto the chip and plasma separation and digitization will commence. In this example, degas loading was stable for up to 30 minutes and MRSA DNA spiked in whole blood was detected within 30 minutes with RPA in one-step using the DS method. No hemolysis or clogging was observed in the DS chip. FIG. 17 shows a graph of the detection of the MRSA Mec A gene DNA added to whole blood at $10^6$ copies/ml and mixed with RPA reagents. FIG. 18A, FIG. 18B and FIG. 18C show fluorescence images (FAM channel) taken with a stereoscope (Zeiss Axiozoom) at t=0 minutes, t=20 minutes and t=50 minutes, respectively. A RPA RT Exo kit was used and n=5.

The one-step digital plasma separation method and apparatus can be used to detect bacterial nucleic acids in whole blood in less than 30 minutes. This is a significant improvement compared to current costly commercial systems, which can take hours of assay time, require trained technicians, and involve costly equipment in centralized labs. The portable DS chip technology may provide a new paradigm for low cost point-of-care blood-based quantitative NA assays in low resource settings such as Africa.

Figure 19:
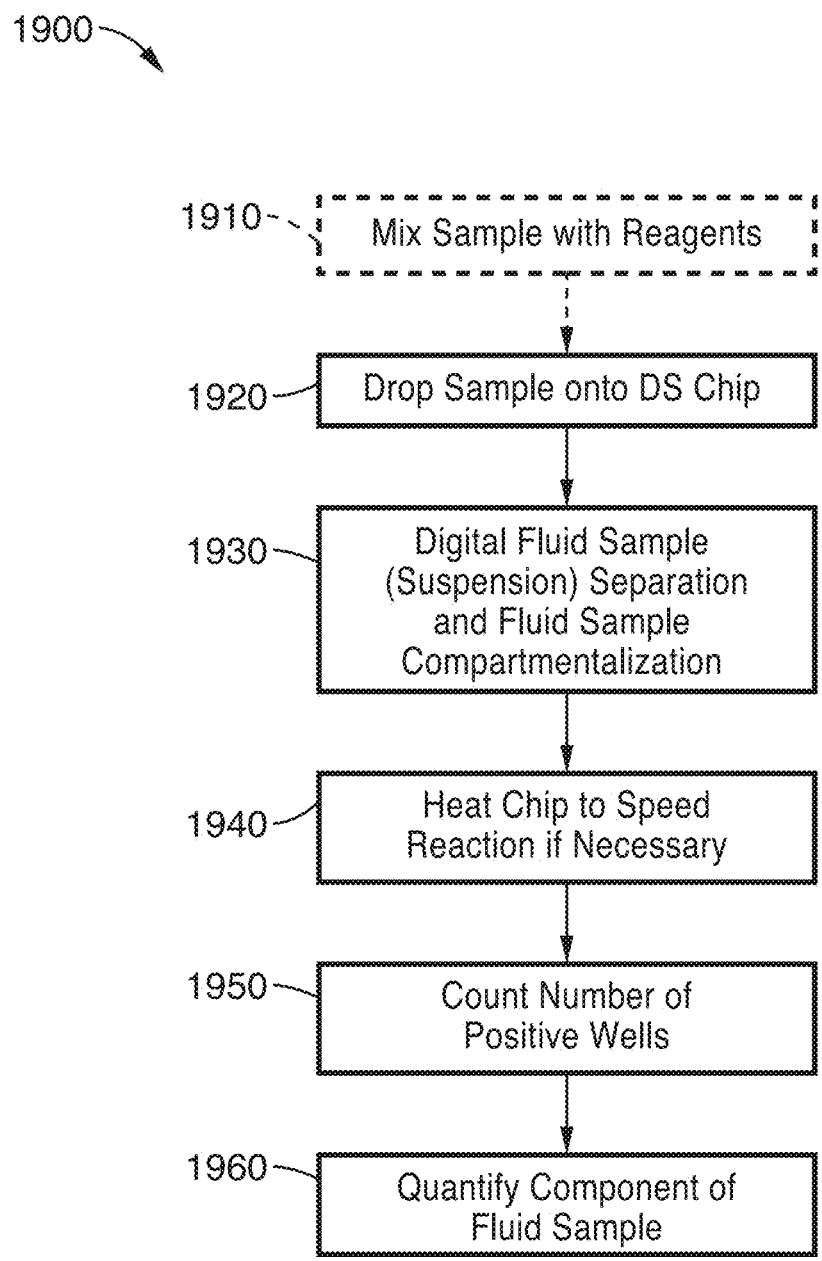
FIG. 19 is a functional flow diagram for an embodiment of methods for use with the DS chip.

FIG. 19 provides a summary flow diagram 1900 for a general embodiment of the simple DS and fluid sample analysis method. This method may be used to detect components in the fluid sample including, but not limited to, nucleic acids, proteins, antibodies, amino acids, peptides, sugars and fats. In the first block 1910, the fluid sample may be mixed with assay reagents before the fluid sample is loaded onto the DS chip.

In alternative embodiments, the assay reagents may also be patterned onto the chip before the sample is loaded. In yet another embodiment, some of the assay reagents may be mixed with the fluid sample before it is loaded onto the chip and some of the assay reagents may be patterned onto the chip. For instance, in Example 1, RPA was used and all of the reagents were mixed with the fluid sample before it was loaded onto the chip except for MgOAc, which was patterned onto the chip in order to initiate NA amplification upon contact with the sample/reagent mix.

In the second block 1920, the user drops the fluid sample onto the chip in the sample inlet. In the next block 1930, the sample suspension moves through the chip and the cliff structures separate the sample suspension to purify the solution from the particles that may interfere with NA amplification, fluorescence readings, etc. An air plug may be used to compartmentalize the skimmed fluid sample once it is in the well of the DS chip. Automatic movement of the sample through the chip may be actuated by degas driven flow. However, if necessary, the chip can include a thumb pump for manually moving the sample through the DS chip or an electric pump, etc. may be used.

The next block 1940 may include a heating step, if necessary to speed the assay reaction. In the next block 1950, the user can count the number of positive wells using a microscope or even a smartphone equipped with simple filters to pick up florescence readings. From this endpoint reading, components in the original sample can be quantified in the last block 1960.

Figure 20:
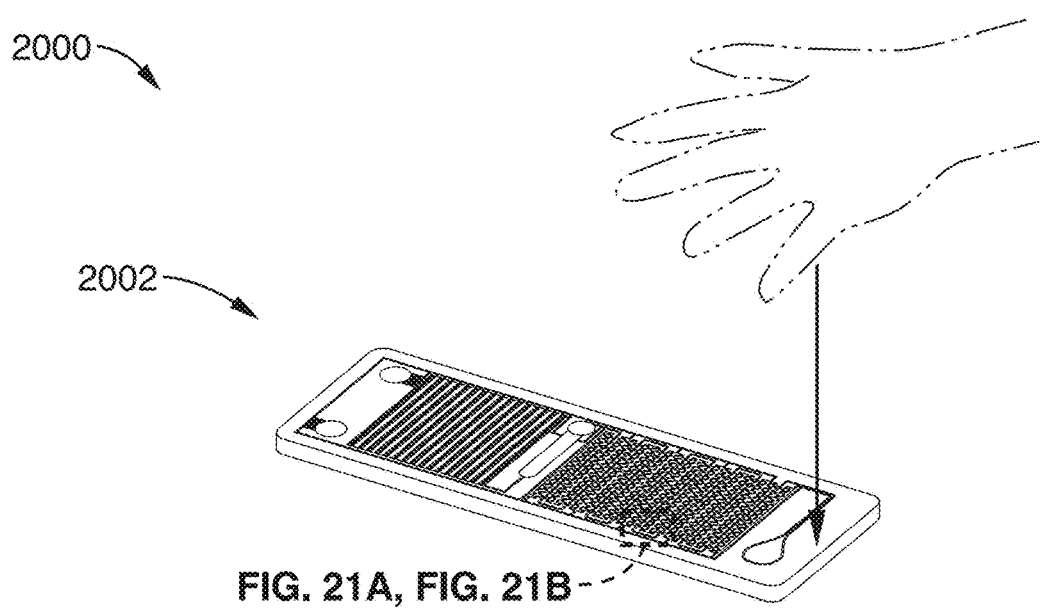
FIG. 20 is a schematic diagram summarizing actions in an embodiment of the presently disclosed method.
Figure 20:
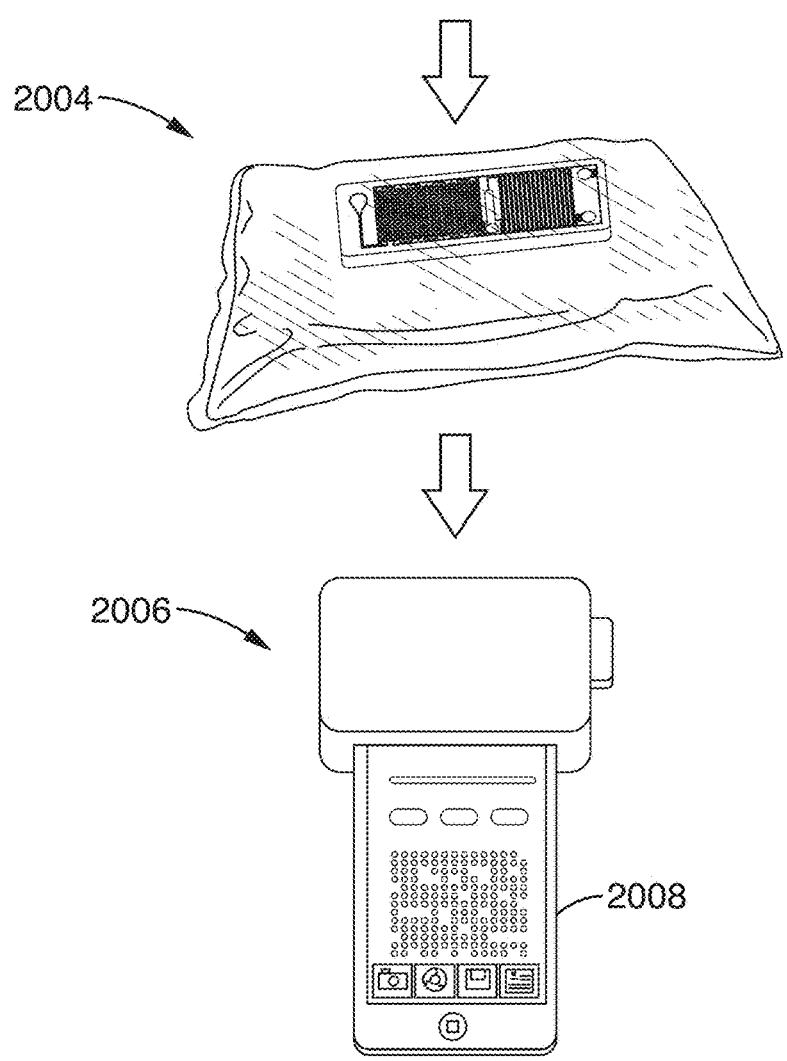
Figure 21A:
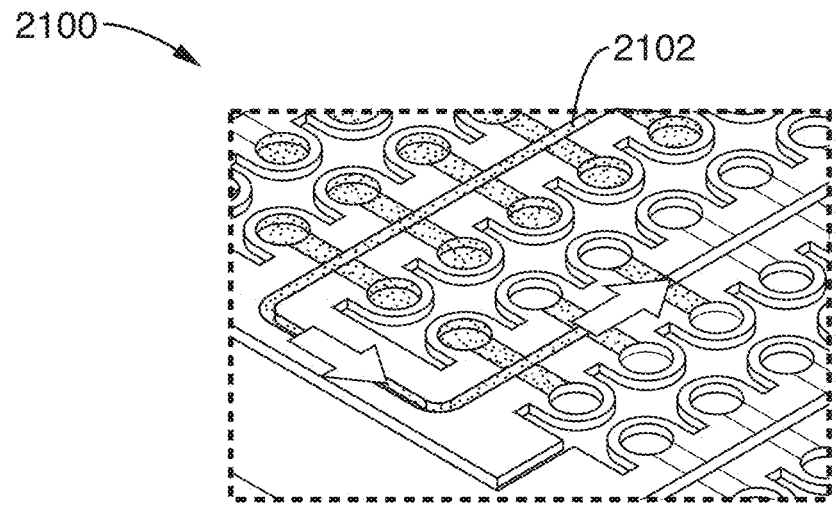
FIG. 21A and FIG. 21B are schematic diagrams of zoomed in views of the sample loading by degas driven flow.
Figure 21B:
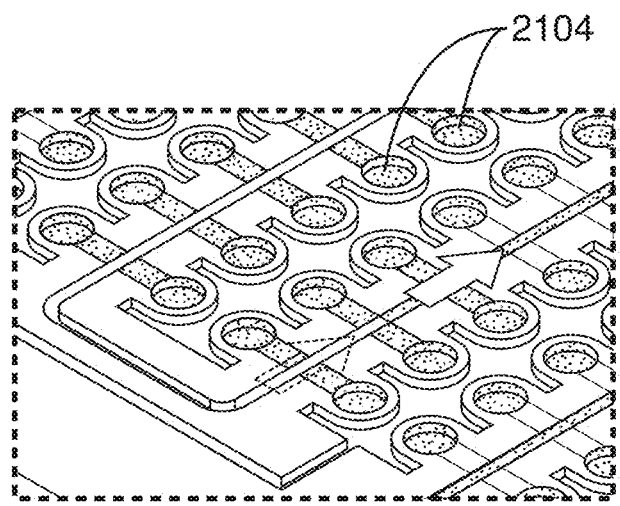

FIG. 20 is a schematic diagram 2000 summarizing an embodiment of the presently disclosed method. In the first panel 2002, a sample is placed onto the DS chip. In the second panel 2004, the DS chip is placed on top of a commercial instant heating pack to accelerate the NA amplification reaction. In the third panel 2006, a smartphone 2008 is used to take the endpoint fluorescence readout. FIG. 21A and FIG. 21B show zoomed in top perspective view schematic diagrams 2100 of the sample 2102 loading by degas driven flow. The solid arrows represent the direction of the sample and the dashed arrows represent the air plug that follows to compartmentalize the digitized sample 2104.

Potential applications for the presently disclosed technology may include but are not limited to: (1) urine analyte detection (e.g. for sexually transmitted diseases), (2) NA titer quantification in blood samples for other viral species (e.g. hepatitis B, hepatitis C, viral hemorrhagic fevers), (3) circulating DNA/RNA quantification in blood samples (e.g. microRNA for cancer diagnostics), (4) blood sepsis quantification for bacteria (e.g. MRSA), (5) blood borne parasite (e.g. malaria) detection in blood samples, (6) general pathogen/analyte quantitative detection in blood samples, (7) multiplexed detection of several diseases at once by patterning different primers into the wells, for example, several strains of HIV and malaria can be detected simultaneously, which could be useful for drug resistance strain identification, (8) TB drug resistance identification in liquefied sputum, (9) water based pathogen detection, and (10) food and beverage quality monitoring.

From the description herein, it will be appreciated that that the present disclosure encompasses multiple embodiments which include, but are not limited to, the following:

1. An apparatus for separating, digitizing and analyzing a fluid sample, the apparatus comprising: (a) a fluidic layer configured to separate a fluid sample into wells for fluid sample analysis, said fluidic layer comprising: (i) a plurality of wells; (ii) a sample inlet that receives the fluid sample; (iii) at least one channel that transports the fluid sample from the sample inlet to one or more wells; (iv) at least one cliff structure positioned in between the channel and each well, configured to skim the fluid sample and prevent particles in the fluid sample from entering the wells, wherein the wells hold skimmed fluid sample for analysis; and (v) an outlet for fluid sample to flow out of the channel; and (b) a blank layer configured to seal the fluidic layer.

2. The apparatus of any preceding embodiment, wherein at least one of the fluidic layer and blank layer are comprised of a gas permeable material, allowing the fluid sample to flow automatically by degas driven flow.

3. The apparatus of any preceding embodiment, wherein the fluidic layer further comprises degas proximal lines coupled to the channels configured to increase the speed of fluid sample flow.

4. The apparatus of any preceding embodiment, wherein the fluid sample is compartmentalized using an air plug that follows behind the fluid sample in the channel.

5. The apparatus of any preceding embodiment, further comprising a thumb pump to move the fluid sample through the apparatus manually.

6. The apparatus of any preceding embodiment: wherein the fluidic layer is a microfluidic layer; wherein the channel is approximately 300 µm deep; wherein the cliff structures are approximately 40 µm deep; and wherein the wells are approximately 300 µm deep.

7. The apparatus of any preceding embodiment, wherein the cliff structures further comprise one or more gap cliff structures within the cliff structures, configured to help speed the separation of particles from solution in the fluid sample.

8. The apparatus of any preceding embodiment, further comprising: a fluorescence detector for detection of components of the fluid sample; wherein said components are labeled with fluorescent labels; and wherein endpoint fluorescence data is collected by either a fluorescence microscope or smartphone equipped with filters.

9. The apparatus of any preceding embodiment: wherein a skimmed fluid sample is analyzed using reagents; wherein one or more of the reagents are patterned on the wells; and wherein one or more of the reagents are mixed with the fluid sample prior to loading the fluid sample into the sample inlet.

10. The apparatus of any preceding embodiment, wherein several different fluid sample components are detected at one time using different reagents in different wells.

11. The apparatus of any preceding embodiment, further comprising a heater.

12. The apparatus of any preceding embodiment, wherein the fluidic layer further comprises a chamber configured to detect less than approximately $10^2$ nucleic acid copies per ml of fluid sample.

13. A method for separating a fluid sample for analysis, the method comprising: (a) obtaining a fluid sample; (b) loading the fluid sample onto a Digital Separation (DS) chip, the DS chip comprising: (1) a fluidic layer configured to separate a fluid sample into wells for fluid sample analysis, said fluidic layer comprising: (i) a plurality of wells; (ii) a sample inlet that receives the fluid sample; (iii) a channel that transports the fluid sample from the sample inlet to the wells; (iv) at least one cliff structure positioned in between the channel and the wells and configured to skim the fluid sample and prevent particles in the fluid sample from entering the wells, said wells holding skimmed fluid samples for analysis; and (v) an outlet for fluid sample to flow out of the channel; and (2) a blank layer configured to seal the fluidic layer.

14. The method of any preceding embodiment, wherein at least one of the fluidic layer and blank layer are comprised of a gas permeable material, allowing the fluid sample to flow automatically by degas driven flow.

15. The method of any preceding embodiment, wherein the fluidic layer further comprises degas proximal lines configured to increase the speed of fluid sample flow.

16. The method of any preceding embodiment, wherein the DS chip further comprises a thumb pump to move fluid sample through the apparatus manually.

17. The method of any preceding embodiment: wherein the sample fluid comprises whole blood; and wherein the cliff structures separate plasma, which flows into the wells, from blood cells.

18. The method of any preceding embodiment, further comprising:
analyzing the skimmed fluid sample by detecting components of the fluid sample; wherein said components are labeled with fluorescent labels; and wherein endpoint fluorescence data is collected by either a fluorescence microscope or smartphone equipped with filters.

19. The method of any preceding embodiment, further comprising: analyzing the skimmed fluid sample using reagents; patterning one or more of the reagents on the wells; and mixing one or more of the reagents with the fluid sample prior to loading the fluid sample into the sample inlet.

20. The method of any preceding embodiment, further comprising: analyzing the skimmed fluid sample using reagents; wherein all of the reagents are either patterned on the wells or mixed with the fluid sample prior to loading into the sample inlet.

21. The method of any preceding embodiment, wherein analysis of the skimmed fluid sample comprises one or more of skimmed fluid sample component amplification and skimmed fluid sample component detection.

22. The method of any preceding embodiment, wherein skimmed fluid sample component detection is quantitative.

23. The method of any preceding embodiment, wherein several different fluid sample components are detected at one time using different reagents in different wells.

24. The method of any preceding embodiment: wherein the skimmed fluid sample components comprise nucleic acids; and wherein nucleic acid analysis comprises isothermal amplification.

25. The method of any preceding embodiment, wherein the DS chip is heated with a chemical heating pack to speed the isothermal nucleic acid amplification.

26. The method of any preceding embodiment, wherein the fluidic layer of the DS chip further comprises a chamber configured to detect less than approximately $10^2$ nucleic acid copies per ml of fluid sample.

27. A gas permeable apparatus for automatically separating, digitizing, compartmentalizing and analyzing a fluid sample, the apparatus comprising: (a) a fluidic layer configured to separate a fluid sample into wells for fluid sample analysis, said fluidic layer comprising: (i) a plurality of wells; (ii) a sample inlet that receives the fluid sample; (iii) at least one channel that transports the fluid sample from the sample inlet to one or more wells, wherein flow of the fluid sample occurs automatically by degas driven flow; (iv) at least one cliff structure positioned in between the channel and each well, configured to skim the fluid sample and prevent particles in the fluid sample from entering the wells, wherein the wells hold skimmed fluid sample for analysis, wherein the skimmed fluid sample is automatically compartmentalized by an air plug that follows behind the sample fluid in the channel, wherein said compartmentalization allows for multiplexed fluid sample analysis within the wells and wherein skimmed fluid sample analysis comprises detection of specific molecules within the skimmed fluid sample, wherein molecules that must be amplified before detection are automatically amplified in the wells before detection; and (v) an outlet for fluid sample to flow out of the channel; and (b) a blank layer configured to seal the fluidic layer; (c) wherein at least one of the fluidic layer and blank layer comprise a gas permeable material for degas driven flow.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for separating, digitizing and analyzing a fluid sample, the apparatus comprising:
    (a) a fluidic layer configured to separate a fluid sample into wells for fluid sample analysis, said fluidic layer comprising:
        (i) a plurality of wells;
        (ii) a sample inlet that receives the fluid sample;
        (iii) a main channel that transports the fluid sample from the sample inlet to one or more wells;
        (iv) a plurality of cross channels each individually coupling the main channel with a dedicated well from among the plurality of wells, wherein the cross channels have a cross-sectional area smaller than a cross-sectional area of the wells and the cross-sectional area of the main channel so as to efficiently compartmentalize the fluid sample into the plurality of wells and prevent backflow of the fluid sample from re-entering the main channel from the wells;
        (v) wherein the wells hold the compartmentalized fluid sample for multiplexed analysis via distinct and independent reactions within each well or distinct and independent targets within each well; and
        (vi) wherein the main channel, plurality of cross channels and plurality of wells have a shape and size to allow for loading, separation and compartmentalization of the fluid sample into the wells in less than 10 minutes; and
    (b) a cover layer configured to seal the fluidic layer;
    (c) wherein at least one of the fluidic layer and cover layer comprise a gas permeable material, allowing the fluid sample to flow automatically into the wells by vacuum diffusion.

2. The apparatus of claim 1, wherein the fluidic layer further comprises degas proximal lines coupled to the main channel to increase the speed of fluid sample flow.

3. The apparatus of claim 1, wherein the fluid sample is compartmentalized using an air plug that follows behind the fluid sample in the main channel.

4. The apparatus of claim 1, further comprising a thumb pump to move the fluid sample through the apparatus manually.

5. The apparatus of claim 1:
    wherein the fluidic layer is a microfluidic layer;
    wherein the main channel is approximately 300 µm deep;
    wherein the cross channels are approximately 40 µm deep; and
    wherein the wells are approximately 300 µm deep.

6. The apparatus of claim 1, wherein the cross channels comprise cliff structures configured to help the separation of particles from solution in the fluid sample.

7. The apparatus of claim 1, further comprising:
    a fluorescence detector for detection of components of the fluid sample;
    wherein said components are labeled with fluorescent labels; and
    wherein endpoint fluorescence data is collected by either a fluorescence microscope or smartphone equipped with filters.

8. The apparatus of claim 1:
    wherein the fluid sample is analyzed using reagents;
    wherein one or more of the reagents are patterned on the wells; and
    wherein one or more of the reagents are mixed with the fluid sample prior to loading the fluid sample into the sample inlet.

9. The apparatus of claim 8, wherein several different fluid sample components are detected at one time using different reagents in different wells.

10. The apparatus of claim 1, further comprising a heater.

11. The apparatus of claim 1, wherein the fluidic layer further comprises a chamber configured to detect less than approximately $10^2$ nucleic acid copies per ml of fluid sample.

12. A gas permeable apparatus for automatically separating, digitizing, compartmentalizing and analyzing a fluid sample, the apparatus comprising:
    (a) a fluidic layer configured to separate a fluid sample into wells for fluid sample analysis, said fluidic layer comprising:
        (i) a plurality of wells;
        (ii) a sample inlet that receives the fluid sample;
        (iii) a main channel that transports the fluid sample from the sample inlet to one or more wells, wherein flow of the fluid sample occurs automatically by vacuum diffusion;
        (iv) a plurality of cross channels each individually coupling the main channel with a dedicated well from among the plurality of wells, wherein the cross channels have a cross-sectional area smaller than a cross-sectional area of the wells and the cross-sectional area of the main channel so as to efficiently compartmentalize the fluid sample into the plurality of wells and prevent backflow of the fluid sample from re-entering the main channel from the wells, wherein the wells hold the compartmentalized fluid sample for multiplexed analysis via distinct and independent reactions within each well or distinct and independent targets within each well, wherein the multiplexed fluid sample analysis comprises detection of specific molecules within the fluid sample, wherein molecules to be amplified before detection are automatically amplified in the wells before detection; and (b) a cover layer configured to seal the fluidic layer;

(c) wherein at least one of the fluidic layer and cover layer comprise a gas permeable material for allowing the fluid sample to flow automatically into the wells by vacuum diffusion; and (d) wherein the main channel, plurality of cross channels and plurality of wells have a shape and size to allow for loading, separation and compartmentalization of the fluid sample into the wells in less than 10 minutes.

13. The apparatus of claim 1, wherein the plurality of wells comprises more than 10 wells.

14. The apparatus of claim 13, wherein the plurality of wells comprises more than 200 wells.

15. The apparatus of claim 12, wherein the plurality of well comprises more than 10 wells.

16. The apparatus of claim 15, wherein the plurality of well comprises more than 200 wells.

17. An apparatus for separating, digitizing and analyzing a fluid sample, the apparatus comprising:

(a) a fluidic layer configured to separate a fluid sample into wells for fluid sample analysis, said fluidic layer comprising:

(i) a plurality of wells;

(ii) a sample inlet that receives the fluid sample;

(iii) a main channel that transports the fluid sample from the sample inlet to one or more wells;

(iv) a plurality of cross channels each individually coupling the main channel with a dedicated well from among the plurality of wells, wherein the cross channels have a cross-sectional area smaller than a cross-sectional area of the main channel and a cross-sectional area of the wells so as to efficiently compartmentalize the fluid sample into the plurality of wells and prevent backflow of the fluid sample from re-entering the main channel from the wells;

(v) wherein the wells hold the compartmentalized fluid sample for multiplexed analysis via distinct and independent reactions within each well or distinct and independent targets within each well; and (b) a cover layer configured to seal the fluidic layer;

(c) wherein at least one of the fluidic layer and cover layer comprise a gas permeable material, allowing the fluid sample to flow automatically into the wells by vacuum diffusion.

18. The apparatus of claim 17, wherein the main channel, plurality of cross channels and plurality of wells have a shape and size to allow for loading, separation and compartmentalization of the fluid sample into the wells in less than 10 minutes.

19. The apparatus of claim 18, wherein the plurality of well comprises more than 200 wells.

* * * * *